US009351977B2

(12) United States Patent
Birrell

(10) Patent No.: US 9,351,977 B2
(45) Date of Patent: May 31, 2016

(54) METHODS OF REDUCING MAMMOGRAPHIC BREAST DENSITY AND/OR BREAST CANCER RISK

(71) Applicant: Chavah Pty Ltd, Stirling (AU)

(72) Inventor: Stephen Nigel Birrell, Piccadilly (AU)

(73) Assignee: CHAVAH PTY LTD., Stirling, South Australia (AU)

( * ) Notice: Subject to any disclaimer, the term of this patent is extended or adjusted under 35 U.S.C. 154(b) by 0 days.

(21) Appl. No.: 14/920,192

(22) Filed: Oct. 22, 2015

(65) Prior Publication Data

US 2016/0113947 A1  Apr. 28, 2016

Related U.S. Application Data

(60) Provisional application No. 62/067,297, filed on Oct. 22, 2014.

(51) Int. Cl.
*A01N 45/00* (2006.01)
*A61K 31/568* (2006.01)
*A61K 31/4196* (2006.01)

(52) U.S. Cl.
CPC ........... *A61K 31/568* (2013.01); *A61K 31/4196* (2013.01)

(58) Field of Classification Search
CPC ................................................... A61K 31/568
USPC ........................................................ 514/171
See application file for complete search history.

(56) References Cited

U.S. PATENT DOCUMENTS

| | | | |
|---|---|---|---|
| 4,147,783 A | 4/1979 | van der Vies | |
| 5,824,286 A | 10/1998 | Hodgen | |
| 5,861,387 A | 1/1999 | Labrie et al. | |
| 6,200,593 B1 | 3/2001 | Place | |
| 6,241,529 B1 | 6/2001 | Place | |
| 6,569,896 B2 | 5/2003 | Dalton et al. | |
| 6,593,313 B2 | 7/2003 | Place et al. | |
| 6,696,432 B1 | 2/2004 | Elliesen et al. | |
| 6,995,284 B2 | 2/2006 | Dalton et al. | |
| 7,772,433 B2 | 8/2010 | Dalton et al. | |
| 8,003,689 B2 | 8/2011 | Veverka | |
| 8,008,348 B2 | 8/2011 | Steiner et al. | |
| 8,980,569 B2 | 3/2015 | Weinberg et al. | |
| 8,980,840 B2 | 3/2015 | Truitt, III et al. | |
| 9,150,501 B2 | 10/2015 | Dalton et al. | |
| 9,168,302 B2 * | 10/2015 | Birrell ................ | A61K 31/4196 |
| 2003/0087885 A1 | 5/2003 | Masini-Eteve et al. | |
| 2004/0191311 A1 | 9/2004 | Liang et al. | |
| 2005/0032750 A1 | 2/2005 | Steiner et al. | |
| 2005/0176692 A1 | 8/2005 | Amory et al. | |
| 2005/0233970 A1 | 10/2005 | Garnick | |
| 2006/0069067 A1 | 3/2006 | Bhatnagar et al. | |
| 2007/0066568 A1 | 3/2007 | Dalton et al. | |
| 2009/0264534 A1 | 10/2009 | Dalton et al. | |
| 2010/0144687 A1 | 6/2010 | Glaser | |
| 2014/0018433 A1 | 1/2014 | Dalton et al. | |
| 2014/0080905 A1 | 3/2014 | Dalton et al. | |
| 2014/0162991 A1 | 6/2014 | Glaser | |

FOREIGN PATENT DOCUMENTS

| | | |
|---|---|---|
| WO | 90/10462 | 9/1990 |
| WO | 94/16709 | 8/1994 |
| WO | 00/69467 | 11/2000 |
| WO | 01/87334 | 11/2001 |
| WO | 02/09721 | 2/2002 |
| WO | 02/30355 | 4/2002 |
| WO | 2004/034978 | 4/2004 |
| WO | 2004/035739 | 4/2004 |
| WO | 2004/064747 | 8/2004 |
| WO | 2005/011705 | 2/2005 |
| WO | 2005/037263 | 4/2005 |
| WO | 2005/070434 | 8/2005 |
| WO | 2007/045027 | 4/2007 |
| WO | 2008/127717 | 4/2008 |
| WO | 2009/036566 | 3/2009 |
| WO | 2010/065358 | 6/2010 |
| WO | 2010/118287 | 10/2010 |
| WO | 2013/067170 | 5/2013 |

OTHER PUBLICATIONS

Glaser et al. Maturitas 76 (2013) 342-349.*
Abu Hashim, H., et al., "*Randomized comparison of superovulation with letrozole vs. clomiphene citrate in an IUI program for women with recently surgically treated minimal to mild endometriosis*," Acta. Obstet. Gynecol. Scand., 91(3), 338-345 (2012) (Epub Jan. 26, 2012).
Alexander, H., et al., "*Proteomic analysis to identify breast cancer biomarkers in nipple aspirate fluid*," Clin. Cancer Res., 10(22), 7500-10 (2004).
Arendt, L.M., et al., "*Working stiff: how obesity boosts cancer risk*," Sci. Transl. Med., 7(301), 301fs34, 3 pages (2015), doi: 10.1126/scitranslmed.aac9446.
Ashbeck, E.L., et al., "*Benign breast biopsy diagnosis and subsequent risk of breast cancer*," Cancer Epidemiol Bionnarkers Prev., 16(3), 467-72 (2007) (Epub Mar. 2, 2007).
Beattie, M.S., "*Endogenous sex hormones, breast cancer risk, and tamoxifen response: an ancillary study in the NSABP Breast Cancer Prevention Trial (P-1)*," J. Natl. Cancer Inst., 98(2), 110-5 (2006).
Beckmann, K.R., et al., "*Impact of hormone replacement therapy use on mammographic screening outcomes*," Cancer Causes Control, 24(7), 1417-1426 (2013) (Epub May 7, 2013).

(Continued)

*Primary Examiner* — Nizal Chandrakumar
(74) *Attorney, Agent, or Firm* — Jones Day

(57) ABSTRACT

The present disclosure is directed to generally methods for treating mammographic breast density and/or breast stiffness in a patient in need thereof, such as a premenopausal or perimenopausal patient, comprising the administration of an effective amount of androgenic agent and an effective amount of an aromatase inhibitor. These methods may also be useful in post-menopausal woman.

14 Claims, 3 Drawing Sheets

(56) References Cited

OTHER PUBLICATIONS

Beer, B., et al., "*Development and validation of a liquid chromatography-tandem mass spectrometry method for the simultaneous quantification of tamoxifen, anastrozole, and letrozole in human plasma and its application to a clinical study*," Anal. Bioanal. Chem., 398(4), 1791-1800 (2010) (Epub Aug. 22, 2010).
Bhasin, S., et al., "*Selective Androgen Receptor Modulators (SARMs) as Function Promoting Therapies*," Curr. Opin. Clin. Nutr. Metab. Care, 12(3), 232-240 (2009).
Birrell, S.N., et al., "*Disruption of androgen receptor signaling by synthetic progestins may increase risk of developing breast cancer*," FASEB J., 21(10), 2285-93 (2007) (Epub Apr. 5, 2007).
Birrell, S.N., et al., "*Combined Hormone Replacement Therapy and Breast Cancer*," Expert Report, 34 pages, dated Apr. 1, 2008.
Bolduc, C., et al., "*Transcriptomic Characterization of the Long-term Dihydrotestosterone Effects in Adipose Tissue*," Obesity, 15(5), 1107-1132 (2007).
Boyd, N.F., et al., "*Mammographic densities and breast cancer risk*," Breast Dis., 10(3-4), 113-126 (1998).
Boyd, N., et al., "*Breast-tissue composition and other risk factors for breast cancer in young women: a cross-sectional study*," Lancet Oncol., 10(6), 569-80 (2009) (Epub Apr. 30, 2009).
Boyd, N.F., et al., "*Mammographic density, response to hormones, and breast cancer risk*," J. Clin. Oncol., 29(22), 2985-2992 (2011) (Epub Jun. 27, 2011).
Boyd, N.F., et al., "*Evidence That Breast Tissue Stiffness Is Associated with Risk of Breast Cancer*," PLoS ONE, 9(7), e100937 (2014) (doi:10.1371/journal.pone.0100937).
Braunstein, G.D., "*Safety of testosterone treatment in postmenopausal women*," Fertil. Steril., 88(1), 1-17 (2007) (Epub May 10, 2007).
Chen, R., et al., "*Antiproliferative effects of anastrozole on MCF-7 human breast cancer cells in vitro are significantly enhanced by combined treatment with testosterone undecanoate*," Mol. Med. Rep., 12(1), 769-775 (2015) (Epub Mar. 4, 2015).
Chiu, S.Y., et al., "*Effect of baseline breast density on breast cancer incidence, stage, mortality, and screening parameters: 25-year follow-up of a Swedish mammographic screening*," Cancer Epidemiol. Biomarkers Prev., 19(5), 1219-1228 (2010) (Epub Apr. 20, 2010).
Chlebowski, R.T., et al., "*Influence of estrogen plus progestin on breast cancer and mammography in healthy postmenopausal women: the Women's Health Initiative Randomized Trial*," JAMA, 289(24), 3243-3253 (2003).
Cilotti, A., et al., "*Male osteoporosis and androgenic therapy: from testosterone to SARMs*," Clin. Cases Miner. Bone Metab., 6(3), 229-233 (2009).
Crandall, C.J., et al., "*Breast tenderness after initiation of conjugated equine estrogens and mammographic density change*," Breast Cancer Res. Treat., 131(3), 969-79 (2012) (Epub Oct. 7, 2011).
Cuzick, J., et al., "*Tamoxifen-Induced Reduction in Mammographic Density and Breast Cancer Risk Reduction: A Nested Case-Control Study*," J. Natl. Cancer Inst., 103(9), 744-752 (2011) (Epub Apr. 11, 2011).
Cuzick, J., et al., "*Impact of preventive therapy on the risk of breast cancer among women with benign breast disease*," Breast, 24 Suppl. 2, S51-S55 (2015).
Dalton, J.T., et al., "*The selective androgen receptor modulator GTx-024 (enobosarm) improves lean body mass and physical function in healthy elderly men and postmenopausal women: results of a double-blind, placebo-controlled phase II trial*," J. Cachexia Sarcopenia Muscle, 2(3), 153-161 (2011) (Epub Aug. 2, 2011).
Davis, S.R., et al., "*Androgen treatment of postmenopausal women*," J. Steroid Biochem. Mol. Biol., 142, 107-114 (2014) (Epub May 29, 2013).
DeFilippis, R.A., et al., "*CD36 Repression Activates a Multicellular Stromal Program Shared by High Mammographic Density and Tumor Tissues*," Cancer Discov., 2(9), 826-839 (2012) (Epub Jul. 9, 2012).
DeFilippis, R.A., et al., "*Stress Signaling from Human Mammary Epithelial Cells Contributes to Phenotypes of Mammographic Density*," Cancer Res., 74(18), 5032-5044 (2014) (Epub Aug. 29, 2014).
Dilley, W.G., et al., "*Androgen Stimulation of Gross Cystic Disease Fluid Protein and Carcinoembryonic Antigen in Patients With Metastatic Breast Carcinoma*," J Natl. Cancer Inst., 70(1), 69-74 (1983).
Dixon, J.M., et al., "*Risk of breast cancer in women with palpable breast cysts: a prospective study. Edinburgh Breast Group*," Lancet, 353(9166), 1742-1745 (1999).
Duhan, N, et al., "*Role of the aromatase inhibitor letrozole in the management of uterine leiomyomas in premenopausal women*," Eur. J. Obstet. Gynecol. Reprod. Biol., 171(2), 329-332 (2013) (Epub Sep. 20, 2013).
Eigeliene, N., et al., "*Androgens Inhibit the Stimulatory Action of 17b-Estradiol on Normal Human Breast Tissue in Explant Cultures*," J. Clin. Endocrinol. Metab., 97(7), E1116-1127 (2012) (Epub Apr. 24, 2012).
European Search Report, dated Aug. 24, 2009 for EP 1945224.
Gao, W., et al., "*Ockham's razor and selective androgen receptor modulators (SARMs): are we overlooking the role of 5alpha-reductase?*" Mol. Interv., 7(1), 10-13 (2007).
Gascard, P., et al., "*Epigenetic and transcriptional determinants of the human breast*," Nat Commun., 6, 6351 (2015), 10 pages, doi: 10.1038/ncomms7351.
Gao, W., et al., "*Expanding the therapeutic use of androgens via selective androgen receptor modulators (SARMs)*," Drug Discov. Today, 12(5-6), 241-248 (2007) (Epub Feb. 7, 2007).
Gaubin, M., et al., "*Potent Inhibition of CD4/TCR-Mediated T Cell Apoptosis by a CD4-Binding Glycoprotein Secreted from Breast Tumor and Seminal Vesicle Cells*," J. Immunol., 162(5), 2631-2638 (1999).
Ghajar, C.M., "*A stiffness-mediated oncogenic hammer*," Sci. Transl. Med., 6(237), 237fs21, 3 pages (2014), doi: 10.1126/scitranslmed.3009154.
Ghosh, S., et al., "*Mechanical phenotype is important for stromal aromatase expression*," Steroids, 76(8), 797-801 (2011) (Epub Mar. 4, 2011).
Giess, C.S., et al., "*Background parenchymal enhancement at breast MR imaging: normal patterns, diagnostic challenges, and potential for false-positive and false-negative interpretation*," Radiographics, 34(1), 234-247 (2014).
Gilliver, S.C., et al., "*5alpha-dihydrotestosterone (DHT) retards wound closure by inhibiting re-epithelialization*," J. Pathol., 217(1), 73-82 (2009).
Glaser, R.L., "*Subcutaneous testosterone-anastrozole implant therapy in breast cancer survivors*," 2010 Breast Cancer Symposium, Abstract 221, (Jan. 2010).
Glaser, R., et al., "*Beneficial effects of testosterone therapy in women measured by the validated Menopause Rating Scale (MRS)*," Maturitas, 68(4), 355-361 (2011) (Epub Dec. 21, 2010).
Glaser, R., et al., "*Testosterone implants in women: pharmacological dosing for a physiologic effect*," Maturitas, 74(2), 179-84 (2013) (Epub Dec. 21, 2012).
Glaser, R., et al., "*Testosterone therapy in women: myths and misconceptions*," Maturitas, 74(3), 230-234 (2013) (Epub Feb. 4, 2013).
Glaser, R.L., et al., "*Reduced breast cancer incidence in women treated with subcutaneous testosterone, or testosterone with anastrozole: a prospective, observational study*," Maturitas, 76(4), 342-349 (2013) (Epub Sep. 10, 2013).
Glaser, R.L., et al., "*Rapid response of breast cancer to neoadjuvant intramammary testosterone-anastrozole therapy: neoadjuvant hormone therapy in breast cancer*," Menopause, 21(6), 673-678 (2014).
Glaser, R.L., et al., "*Testosterone and breast cancer prevention*," Maturitas, 82(3), 291-295 (2015) (Epub Jun. 24, 2015).
Golatta, M., et al., "*Evaluation of virtual touch tissue imaging quantification, a new shear wave velocity imaging method, for breast lesion assessment by ultrasound*," Biomed. Res. Int., 2014, 960262 (7 pages) (2014) (Epub Mar. 31, 2014).
Goss, P.E., et al. "*Anastrozole: A New Selective Nonsteroidal Aromatase Inhibitor*," Oncology, 11(11), 1697-1703 (1997)—Abstract only (Complete copy from www.cancernetwork.com).
Goss, P.E., et al., "*Chemoprevention with aromatase inhibitors—trial strategies*," J. Steroid Biochem. Mol. Biol., 79(1-5), 143-149 (2001).

(56) References Cited

OTHER PUBLICATIONS

Gunter, M.J., et al., "*Circulating Adipokines and Inflammatory Markers and Postmenopausal Breast Cancer Risk*," J. Natl. Cancer Inst., 107(9), 10 pages, (2015) doi: 10.1093/jnci/djv169.

Haagensen, D.E., et al., "*Breast gross cystic disease fluid analysis. I. Isolation and radioimmunoassay for a major component protein*," J. Natl. Cancer Inst., 62(2), 239-247 (1979).

Hodgson, M.C., et al., "*Reduced Androgen Receptor Expression Accelerates the Onset of ERBB2 Induced Breast Tumors in Female Mice*," PLoS ONE, 8(4), e60455, pp. 1-12 (2013) (doi:10.1371/journal.pone.0060455).

Hubalek, M., et al., "*Does Obesity Interfere With Anastrozole Treatment? Positive Association Between Body Mass Index and Anastrozole Plasma Levels*," Clin. Breast Cancer, 14(4), 291-296 (2014) (Epub Dec. 27, 2013).

International Search Report and Written Opinion, dated Jan. 3, 2007 for PCT/AU2006/001539.

International Search Report and Written Opinion, dated Dec. 16, 2015, for PCT/AU2015/000633.

Iobagiu, C., et al., "*Loss of heterozygosity in tumor tissue in hormonal receptor genes is associated with poor prognostic criteria in breast cancer*," Cancer Genet., 208(4), 135-142 (2015) (Epub Feb. 20, 2015).

Ironside, A.J., et al., "*Stromal characteristics may hold the key to mammographic density: The evidence to date*," Oncotarget, 13 pages, (2016) doi: 10.18632/oncotarget.6912.

Japanese Office Action dated Jul. 3, 2012 for Application No. 2008-535845 with English Translation.

Javed, A., "*Development of the human breast*," Semin. Plast. Surg., 27(1), 5-12 (2013).

Kass, L., et al., "*Mammary epithelial cell: influence of extracellular matrix composition and organization during development and tumorigenesis*," Int. J. Biochem. Cell Biol., 39(11), 1987-1994 (2007) (Epub Jul. 19, 2007).

Li, C.I., et al., "*Effect of depo-medroxyprogesterone acetate on breast cancer risk among women 20 to 44 years of age*," Cancer Res., 72(8), 2028-2035 (2012) (Epub Feb. 27, 2012).

Li, X., et al, "*Determination of the Elasticity of Breast Tissue during the Menstrual Cycle Using Real-Time Shear Wave Elastography*," Ultrasound Med. Biol., 41(12), 3140-3147 (2015) (Epub Sep. 26, 2015).

Lienart, V., et al., "*Effect of preventive hormonal therapy on breast density: a systematic qualitative review*," ScientificWorldJournal, 2014, 942386 (24 pages) (2014) (Epub Apr. 27, 2014).

Lillie, E.O., et al., "*Polymorphism in the Androgen Receptor and Mammographic Density in Women Taking and Not Taking Estrogen and Progestin Therapy*", Cancer Res., 64(4), 1237-1241 (2004).

Lombard, J.M., et al., "*Aromatase inhibitor induced musculoskeletal syndrome: a significant problem with limited treatment options*," Support Care Cancer, pp. 1-8 (2015) (DOI 10.1007/s00520-015-3001-5).

Lowdon, R.F., et al., "*Regulatory Network Decoded from Epigenomes of Surface Ectoderm-Derived Cell Types*," Nat. Commun., 5, 5442, 27 pages (2014), doi:10.1038/ncomms6442.

Lundin, K.B., et al., "*Androgen receptor genotypes predict response to endocrine treatment in breast cancer patients*," Br. J. Cancer, 105(11), 1676-1683 (2011) (Epub Oct. 27, 2011).

Mocellin, S., et al., "*Breast Cancer Chemoprevention: A Network Meta-Analysis of Randomized Controlled Trials*," J. Natl. Cancer Inst., 108(2), 9 pages (2016) doi: 10.1093/jnci/djv318.

Mockus, M., et al., "*First Pregnancy Characteristics, Postmenopausal Breast Density, and Salivary Sex Hormone Levels in a Population at High Risk for Breast Cancer*," BBA Clin., 3, 189-195 (2015).

Moshina, N., et al., "*Mammographic density and histopathologic characteristics of screen-detected tumors in the Norwegian Breast Cancer Screening Program*," Acta Radiol. Open, 4(9), 2058460115604340 (4 pages) (2015).

Mousa, N.A., et al. "*Aromatase inhibitors and mammographic breast density in postmenopausal women receiving hormone therapy*," Menopause, 15(5), 875-884 (2008).pdf.

Narayanan, R., et al., "*Selective Androgen Receptor Modulators (SARMs) Negatively Regulate Triple-Negative Breast Cancer Growth and Epithelial:Mesenchymal Stem Cell Signaling*," PLoS One, 9(7), e103202 (12 pages) (2014).

Ng, K.H., et al., "*Vision 20/20: Mammographic breast density and its clinical applications*," Med. Phys., 42(12), 7059-7077 (2015).

Niravath, P., "*Aromatase inhibitor-induced arthralgia: a review*," Ann. Oncol., 24(6), 1443-1449 (2013) (Epub Mar. 6, 2013).

Ochnik, A.M., et al., "*Antiandrogenic actions of medroxyprogesterone acetate on epithelial cells within normal human breast tissues cultured ex vivo*," Menopause, 21(1), 79-88 (2014).

Olsen, N.J., et al., "*Evidence that androgens modulate human thymic T cell output*," J. Investig. Med., 59(1), 32-35 (2011).

Ozkaya, E., et al., "*Is hyperandrogenemia protective for fibrocystic breast disease in PCOS?*", Gynecol. Endocrinol., 28(6), 468-71 (2012) (Epub Nov. 21, 2011).

Parsanezhad, M.E., et al., "*A randomized, controlled clinical trial comparing the effects of aromatase inhibitor (letrozole) and gonadotropin-releasing hormone agonist (triptorelin) on uterine leiomyoma volume and hormonal status*," Fertil Steril., 93(1),192-198 (2010) (Epub Jan. 9, 2009).

Peres, J., "*Why Is Breast Cancer Chemoprevention Such a Hard Sell?*" J. Natl. Cancer Inst., 106(5), 4-6 (2014).

Pettersson, A., et al., "*Mammographic density phenotypes and risk of breast cancer: a meta-analysis*," J. Natl. Cancer Inst., 106(5), 11 pages (2014) doi: 10.1093/jnci/dju078.

Pike, M.C., et al., "*Mammographic density, MRI background parenchymal enhancement and breast cancer risk*," Ann. Oncol., 24 Suppl 8, viii37-viii41 (2013), doi: 10.1093/annonc/mdt310.

Plourde, P.V., et al., "*Arimidex: a potent and selective fourth-generation aromatase inhibitor*," Breast Cancer Res. Treat., 30(1), 103-111 (1994).

Rhoden, E.L., et al., "*Treatment of testosterone-induced gynecomastia with the aromatase inhibitor, anastrozole*," International Journal of Impotence Research, 16, 95-97 (2004).

Rinsho, et al., Japanese Journal of Clinical and Experimental Medicine, 70(11), 3428-3433 (1993).

Robinson, J.L.L., et al., "*Androgen receptor driven transcription in molecular apocrine breast cancer is mediated by FoxA1*," EMBO J., 30(15), 3019-3027 (Jun. 24, 2011).

Robinson, J.L.L., et al., "*FoxA1 is a key mediator of hormonal response in breast and prostate cancer*," Front. Endocrin., 3(68), 1-6 (2012) (doi: 10.3389/fendo.2012.00068).

Santen, Richard J., "*Recent Progress in Development of Aromatase Inhibitors*," J. Steroid Biochem. Molec. Biol., 37(6), 1029-1035 (1990).

Scurr, J., et al., "*The Prevalence, Severity, and Impact of Breast Pain in the General Population*," Breast J., 20(5), 508-13 (2014) (Epub Jul. 7, 2014).

Smith, J., et al. "*A pilot study of letrozole for one year in women at enhanced risk of developing breast cancer: effects on mammographic density*," Anticancer Res., 32(4), 1327-1331 (2012).

Somboonporn, et al., "*Postmenopausal Testosterone Therapy and Breast Cancer Risk*," Maturitas, 49, 267-275 (2004).

Tarone, R.E., et al., "*Breast Reduction Surgery and Breast Cancer Risk: Does Reduction Mammaplasty Have a Role in Primary Prevention Strategies for Women at High Risk of Breast Cancer?*", Plast. Reconstr. Surg., 113(7), 2104-10 (2004).

The Merck Index, 13th ed., Merck & Co., Inc. (2001), Entry Nos. 632 (p. 105), 3944 (p. 692) and 9255 (p. 1638).

The North American Menopause Society, Menopause: The Journal of The North American Menopause Society, 12(5), 497-511 (2005).

Tiwary, B., et al., "*Parallel Evolution between Aromatase and Androgen Receptor in the Animal Kingdom*," Mol. Biol. Evol., 26(1), 123-129 (2009) (Epub Oct. 20, 2008).

Vachon, C.M., et al., "*Mammographic breast density response to aromatase inhibition*," Clin. Cancer Res., 19(8), 2144-2153 (2013) (Epub Mar. 6, 2013).

(56) References Cited

OTHER PUBLICATIONS

Viacava, P., et al., "*Spectrum of GCDFP-15 expression in human fetal and adult normal tissues*," Virchows Arch., 432(3), 255-260 (1998).

Wanders, J.O., et al., "*The effect of weight change on changes in breast density measures over menopause in a breast cancer screening cohort*," Breast Cancer Res., 17, 74 (8 pages) (2015).

Warwick, J., et al., "*Mammographic breast density refines Tyrer-Cuzick estimates of breast cancer risk in high-risk women: findings from the placebo arm of the International Breast Cancer Intervention Study I*," Breast Cancer Res., 16(5), 451 (6 pages) (2014).

Wasaff, Barbara, "*Current Status of Hormonal Treatments for Metastatic Breast Cancer in Postmenopausal Women*," Oncol. Nurs. Forum, 24(9), 1515-1520 (1997).

Wu, S., et al., "*Quantitative assessment of background parenchymal enhancement in breast MRI predicts response to risk-reducing salpingo-oophorectomy: preliminary evaluation in a cohort of BRCA1/2 mutation carriers*," Breast Cancer Res., 17, 67 (11 pages) (2015), doi: 10.1186/s13058-015-0577-0.

Yang, Y., et al., "*Influence of factors on mammographic density in premenopausal Chinese women*," Eur. J. Cancer Prev., Jun. 11, 2015 (Epub ahead of print), 6 pages.

Youk, J.H., et al., "*Quantitative Lesion-to-Fat Elasticity Ratio Measured by Shear-Wave Elastography for Breast Mass: Which Area Should Be Selected as the Fat Reference?*" PLoS One, 10(9), e0138074, 11 pages (2015), doi: 10.1371/journal.pone.0138074.

Zhong, A., et al., "*Stromal-epithelial cell interactions and alteration of branching morphogenesis in macromastic mammary glands*," J. Cell Mol. Med., 18(7), 1257-1266 (2014) (Epub Apr. 10, 2014).

Zhou, J. et al., "*Testosterone inhibits estrogen-induced mammary epithelial proliferation and suppresses estrogen receptor expression*," FASEB J., 14(12), 1725-1730 (2000).

Zimmerman, Y., et al., "*The effect of combined oral contraception on testosterone levels in healthy women: a systematic review and meta-analysis*," Hum. Reprod. Update, 20(1), 76-105 (2014) (Epub Sep. 29, 2013).

\* cited by examiner

Figure 3A

Estimation of radius (R1) from measure of breast volume

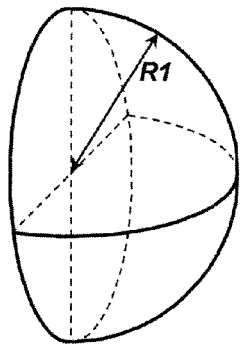

Volume – hemisphere ⟶ $R_{volume}$ = R1 (cm)

$$\text{Volume} = \frac{1}{2}\left(\frac{4}{3}\pi R_{volume}^3\right)$$

Figure 3B

Estimation of radius (R2) from measure of compressed breast area

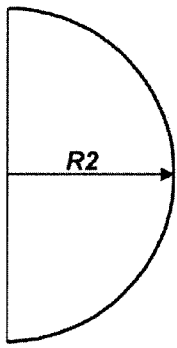

Area – semicircle ⟶ $R_{compressed\ area}$ = R2 (cm)

$$\text{Area} = \frac{1}{2}\left(\pi R_{compressed\ area}^2\right)$$

Figure 3C

Calculation of breast stiffness from R1, R2 and compression force

Compression force = F (dN)

$$\text{Stiffness} \propto \frac{F}{R2-R1}\ (N/cm)$$

METHODS OF REDUCING MAMMOGRAPHIC BREAST DENSITY AND/OR BREAST CANCER RISK

CROSS REFERENCE TO RELATED APPLICATION

This application claims the benefit of U.S. provisional application No. 62/067,297, entitled "Methods of Reducing Mammographic Breast Density and/or Breast Cancer Risk", filed Oct. 22, 2014. This application, in its entirety, is incorporated herein by reference.

FIELD

The present disclosure is directed generally to methods for reducing mammographic breast density and/or breast stiffness in warm blooded animals, for example, in a woman, such as a premenopausal, a perimenopausal, or a post-menopausal woman, comprising the administration of an effective amount of androgenic agent and an effective amount of an aromatase inhibitor. The present disclosure is also directed to reducing the risk of breast cancer in warm blooded animals by administering an effective amount of androgenic agent and an effective amount of an aromatase inhibitor to certain warm blooded animals with unacceptable breast density and/or breast stiffness.

RELATED REFERENCES

Boyd, et al., "Evidence that Breast Tissue Stiffness is Associated with Risk of Breast Cancer," 9(7), e100937, pp 1-8 (July 2014).

D'Orsi C J, Sickles E A, Mendelson E B, Morris E A et al. (2013). *ACR BI-RADS® Atlas, Breast Imaging Reporting and Data System*. Reston, Va.: American College of Radiology.

These references, in their entirety, are incorporated herein by reference.

BACKGROUND

It has been estimated that 43% of women in the United States of America between 40 and 75 years of age have mammographic breast density (MBD) which is categorized as high, e.g., having a Breast Imaging-Reporting and Data System (BIRADS) score of 3 and 4 (or c and d). The American Cancer Foundation has suggested that this high breast density is a significant risk factor for the development of breast cancer. MBD may not be related to how a breast feels to palpation; but rather how it looks on the mammogram. Therefore a woman could be oblivious to how dense her breast tissue is and how high a risk-factor this is for developing breast cancer.

Traditionally, therapeutic intervention for the peri-menopausal transition is either a low dose combination oral contraceptive or continuous estradiol and a synthetic progestin delivery system to protect the uterus from both increased endometrial cancer risk and unwanted uterine bleeding. The present inventors believe that these are inappropriate treatments for women with high breast density and/or breast stiffness as they reduce an already precarious testosterone level and increase breast density and/or breast stiffness. However these are the current recommendations of the Menopause Society of North America and the Menopause Society of Australia.

While hormonal prevention strategy studies have demonstrated that anti-estrogens such as tamoxifen and aromatas inhibitors, as well as selective estrogen receptor modulators, may reduce the incidence of breast cancer, none of these have widespread use due to the side-effects associated with the menopausal symptoms induced by these therapies.

Although the mechanisms by which breast density and/or breast stiffness affects breast cancer risk are not well understood, it is estimated that a significant percentage of breast cancers are attributable to unacceptable levels of breast density and/or breast stiffness.

To date there has been no successful prescribed method for the reduction of mammographic breast density and/or breast stiffness and therefore, the reduction in the instances of breast cancer associated with such conditions in certain women.

The present disclosure is directed to overcome and/or ameliorate at least one or more of the disadvantages of the prior art, as will become apparent from the discussion herein. The present disclosure also provides other advantages and/or improvements as discussed herein.

DEFINITIONS

Terms are used herein as generally used in the art, unless otherwise defined in the following:

The term "adjuvant therapy" may include adjuvant, neo-adjuvant and/or palliative therapy.

The term "androgenic agent" is understood to mean a chemical that increases androgenic activity or synthesis. Typically, an androgenic agent is a steroid hormone that binds with high affinity (in the pM or nM range) and specificity to its intracellular mediator, the androgen receptor, to stimulate transactivation activity and thus regulate the expression of target genes. Examples are provided herein.

The term "aromatase inhibitor" is understood to mean a chemical compound or polypeptide that blocks and/or inhibits the activity of aromatase which is an enzyme that converts androgens to estrogens. Examples are provided herein.

The term "breast cancer" is understood to mean a malignant proliferation of epithelial cells lining the ducts or lobules of the breast.

The term "breast stiffness" is understood to mean, in its broadest sense, as the measurement of the resistance of a breast to deformation. Factors that may influence the degree of breast stiffness include, but is not limited to, physical forces generated by interactions between cells and between cells and the extracellular matrix, the number of cells and the extent of collagen present in the breast, and the degree of proteoglycan expression. One example of measuring breast stiffness includes the use of the formula force/deformation (dN/cm), where dN denotes deca-Newtons and cm centimeters, wherein the deformation may be determined as the difference between the radius of the mammographic area semicircle and the radius of the volumetric hemisphere, and the the compression force is recorded from the mammogram, such as a digital mammogram. (Boyd, et al., "Evidence that Breast Tissue Stiffness is Associated with Risk of Breast Cancer," 9(7), e100937, pp 1-8 (July 2014)).

The term "breast tissue" is understood to mean the collection of epithelial cells, stromal cells, extracellular matrix, and/or migratory cells, located within and in the vicinity of the breast.

The term "effective amount" or "pharmaceutically effective amount" of an agent or compound as provided herein is understood to mean a sufficient amount of the agent or compound to provide the desired therapeutic effect and is non-toxic, has an acceptable nontoxic profile and/or an acceptable side effects profile. The amount required may vary from patient to patient, depending, for example, on age, general condition of the patient, the severity of the condition being treated, the particular agent or compound administered one or more combinations of these factors and the like. An appropriate "effective amount" typically in an individual case may be determined by one of ordinary skill in the art by reference to the pertinent texts and literature and/or using routine experimentation.

The term "mammographic breast density" or "MBD" is understood to mean a qualitative estimate of the proportion or percentage of radiopaque, or fibroglandular ("dense") elements/tissue in the breast relative to total breast area (via 2-D determination) or volume (via 3-D determination). Mammographic breast density may be determined by various methods, including but not limited to, mammography, digital mammography, magnetic resonance imaging (MRI), ultrasound, digital breast tomosynthesis (DBT), virtual touch tissue imaging quantification (VTIQ), and combinations thereof. MBD may be qualitatively assessed, via 2-D determinations and/or using the BIRADS density categories, with 1 (or a) being least dense and 4 (or d) being the most dense. MBD may also be qualitatively and/or quantitatively assessed via 3-D determinations and/or using volumetric measurements of the breast, such as determining the volumetric breast density, which is the proportion of fibroglandular (dense) tissue relative to the total volume of tissue in the breast (e.g., fibroglandular (dense) tissue and fat in the breast). Assessments of MBD via 3-D determinations can also account for heterogeneity of dense tissue within the breast. There are several tests that may be used to measure MBD, including but not limited to, VOLPARA, QUANTRA, CUMULUS, and methods taking into account the volume of fibroglandular tissue ($cm^3$) and volume of breast ($cm^3$).

The term "peri-menopause" or "menopausal transition" is understood to mean the period of time around menopause during which a woman's body makes its natural transition toward permanent infertility (menopause). Women may start perimenopause at different ages, and may notice signs of progression toward menopause, such as menstrual irregularity, during their 40's, or even as early as their mid-30's. During perimenopause, estrogen levels may rise and fall unevenly, menstrual cycles may lengthen or shorten, and menstrual cycles may begin in which the ovaries do not release an egg (ovulate). During perimenopause, other menopause-like symptoms may be experienced, including, but not limited to, hot flashes, sleep problems, and/or vaginal dryness.

The term "perimenopausal symptoms" is understood to include, but is not limited to, menstrual irregularity; hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, or a decrease in high-density lipoprotein (HDL) cholesterol and combinations thereof.

The term "pharmaceutically acceptable" is understood to mean those compounds, agents, materials, compositions, excipients, and/or dosage forms that are, within the scope of sound medical judgment, suitable for contact with the tissues of human beings and/or animals without excessive toxicity, irritation, allergic response, or other problems or complications commensurate with a reasonable benefit and/or risk ratio.

The term "post-menopausal woman" is understood to include not only a woman of advanced age who has passed through menopause, but also a woman who has been hysterectomized or for some other reason has suppressed estrogen production, such as one who has undergone long-term administration of corticosteroids, suffer from Cushions' syndrome or have gonadal dysgenesis.

The term "selective androgenic receptor modulator" or "SARM" is an androgenic agent and is understood to include an agonist, or partial agonist, of androgen receptor in the cell wall, cytoplasm or nucleus of a cellular element found within the breast (e.g., stromal, epithelial, adipocyte, or cellular element that may enter the breast as a migratory element, such as a macrophage or lymphocyte.

The term "subject" is an animal including the human species that is treatable with the compositions, methods and kits of the present disclosure. The term "subject" or "subjects" is intended to refer to both the male and female gender unless one gender is specifically indicated.

The term "treatment" or "therapy" as used herein includes preventative (e.g., prophylactic) treatment and/or palliative treatment and "treating" as used herein refers to the act of providing preventative and/or palliative treatment.

It will be apparent to one skilled in the art, in view of the following detailed description and the claims appended hereto, that various substitutions and/or modifications may be made to the present disclosure without departing from the scope of the inventions as claimed.

SUMMARY

Certain embodiments are directed to a method of treating mammographic breast density and/or breast stiffness in a patient in need thereof, comprising administering to the patient: i) an effective amount of androgenic agent; and ii) an effective amount of an aromatase inhibitor.

Certain embodiments are directed to a method of reducing mammographic breast density in a patient having a breast with a mammographic breast density of 7.5% or greater, comprising administering to the patient: i) an effective amount of androgenic agent; and ii) an effective amount of an aromatase inhibitor.

Certain embodiments are directed to a method of treating mammographic breast density in a patient having a breast with a BIRADS score of 3 or 4 (or c or d), comprising administering to the patient: i) an effective amount of androgenic agent; and ii) an effective amount of an aromatase inhibitor.

Certain embodiments are directed to a method of inducing breast involution in a patient in need thereof, comprising administering to the patient: i) an effective amount of androgenic agent; and ii) an effective amount of an aromatase inhibitor.

Certain embodiments are directed to a method of inducing net cell death over proliferation in a breast of a patient in need thereof, comprising administering to the patient: i) an effective amount of androgenic agent; and ii) an effective amount of an aromatase inhibitor.

Certain embodiments are directed to a method of inducing net extracellular matrix degradation over development of extracellular matrix in a breast of a patient in need thereof, comprising administering to the patient: i) an effective amount of androgenic agent; and ii) an effective amount of an aromatase inhibitor.

Certain embodiments are directed to a method of reversing cell number and mammographic breast density in a breast of a peri-menopausal patient, comprising administering to the patient: i) an effective amount of androgenic agent; and ii) an effective amount of an aromatase inhibitor.

Certain embodiments are directed to a method of reducing mammographic breast density and peri-menopausal symptoms in a patient in need thereof, comprising administering to the patient an effective amount of androgenic agent.

Certain embodiments are directed to a method of reducing mammographic breast density and peri-menopausal symptoms in a patient in need thereof, comprising administering to the patient: i) an effective amount of androgenic agent; and ii) an effective amount of an aromatase inhibitor.

The embodiments disclosed herein may optionally include a pharmaceutically acceptable excipient and/or carrier Certain embodiments are directed to methods for the identification of women in the peri-menopause and/or premenopause who have mammographically dense breast tissue and/or breast stiffness, as described by an appropriate mathematical algorithm produced from mammographic images. These identified women may then be provided with a prophylactic and an effective amount of androgenic agent and/or an effective amount of an aromatase inhibitor. For example, in certain embodiments, the composition may be administered by subcutaneous application.

This summary is not intended to be limiting as to the embodiments disclosed herein and other embodiments are disclosed in this specification. In addition, limitations of one embodiment may be combined with limitations of other embodiments to form additional embodiments.

DETAILED DESCRIPTION OF THE DRAWINGS

For a better understanding of the disclosure, and to show more clearly how it may be carried into effect according to one or more embodiments thereof, reference will now be made, by way of example, to the accompanying figures.

FIG. 3A is a graphical and formulaic expression to estimate the radius (R1) from the measure of breast volume.

FIG. 3B is a graphical and formulaic expression to estimate the radius (R2) from the measure of compressed breast area.

FIG. 3C is a calculation of breast stiffness from R1, R2, and compression force.

DETAILED DESCRIPTION

Figure 1:
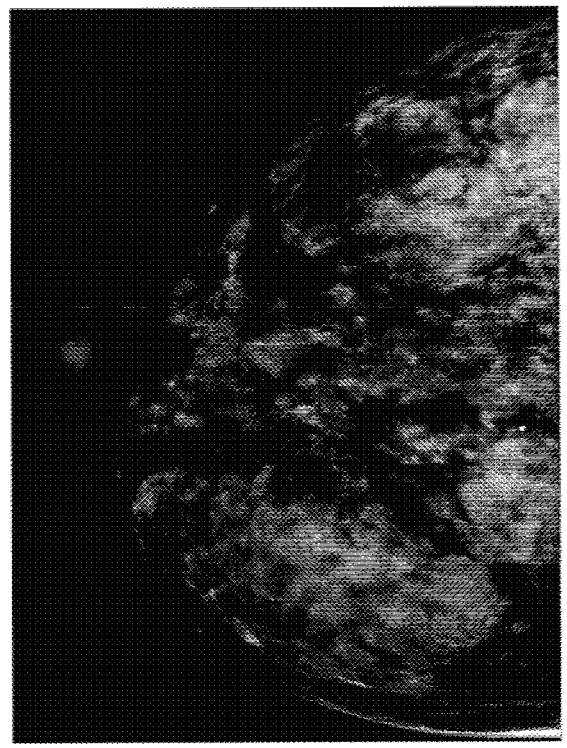
FIG. 1 is a mammogram of a patient's breast immediately before treatment (i.e., at presentation).

The following description is provided in relation to several embodiments that may share common characteristics and features. It is to be understood that one or more features of one embodiment may be combined with one or more features of other embodiments. In addition, a single feature or combination of features in certain of the embodiments may constitute additional embodiments. Specific structural and functional details disclosed herein are not to be interpreted as limiting, but merely as a representative basis for teaching one skilled in the art to variously employ the disclosed embodiments and variations of those embodiments.

The subject headings used in the detailed description are included only for the ease of reference of the reader and should not be used to limit the subject matter found throughout the disclosure or the claims. The subject headings should not be used in construing the scope of the claims or the claim limitations.

The present inventors have discovered high breast density and/or breast stiffness is not normal, rather it is pathological; and it is something which may be addressed by effective amounts of an effective amount of androgenic agent and/or an effective amount of an aromatase inhibitor rather than being treated as a lifestyle modification (e.g. diet exercise) which has not proven to be successful in premenopausal and/or peri-menopausal women. Certain embodiments are directed to methods for identification of mammographically dense breast tissue and/or breast stiffness in premenopausal and/or peri-menopausal women, and providing methods of providing an intervention composition to reduce this mammographic density and/or breast stiffness.

The present disclosure is directed to a number of methods for effecting mammographic breast density and/or breast stiffness by use in warm blooded animals of an effective amount of androgenic agent and/or an effective amount of an aromatase inhibitor.

Certain of the disclosed embodiments may be used, for example, in a premenopausal or perimenopausal woman.

The present disclosure is also directed to reducing the risk of breast cancer in warm blooded animals by administering an effective amount of androgenic agent and an effective amount of an aromatase inhibitor to certain warm blooded animals with unacceptable breast density and/or breast stiffness.

Certain embodiments are directed to methods for reducing and/or treating mammographic breast density and/or breast stiffness in a patient in need thereof.

Certain embodiments are directed to methods for reducing and/or treating mammographic breast density and/or breast stiffness in a patient in need thereof, without inducing peri-menopausal side effects.

Certain embodiments are directed to methods for reducing and/or treating mammographic breast density and/or breast stiffness in a patient in need thereof, without inducing post-menopausal side effects.

Certain embodiments are directed to methods for reducing and/or treating mammographic breast density and/or breast stiffness in a patient in need thereof, wherein the method further decreases the virulence of a breast cancer that develops in the patient.

Certain embodiments are directed to methods for reducing and/or treating mammographic breast density and/or breast stiffness in a patient in need thereof, wherein the method further reduces the progression of a breast cancer that develops in the patient.

Certain embodiments are directed to methods for reducing and/or treating mammographic breast density and/or breast stiffness in a patient in need thereof, wherein the breast density is reduced by at least 20% over a period of 1-5 years or the breast stiffness is reduced by at least 10% over a period of 1-5 years.

Certain embodiments are directed to methods for reducing and/or treating mammographic breast stiffness in a patient in need thereof, wherein the breast stiffness is reduced by at least 20% over a period of 1-5 years or the breast stiffness is reduced by at least 10% over a period of 1-5 years.

Certain embodiments are directed to methods for reducing and/or treating mammographic breast density and/or breast stiffness in a patient in need thereof, wherein the breast density is reduced by at least 2%, 5%, 10%, 20% or 30% over a period of time.

Certain embodiments are directed to methods for reducing and/or treating mammographic breast stiffness in a patient in need thereof, wherein the breast stiffness is reduced by at least 2%, 5%, 10%, 20% or 30% over a period of time.

Certain embodiments are directed to methods of reducing mammographic breast density in a patient having a breast with a mammographic breast density of 7.5% or greater.

Certain embodiments are directed to methods of reducing and/or treating mammographic breast density in a patient having a breast with a BIRADS score of 3 or 4 (or c or d).

Certain embodiments are directed to methods of inducing breast involution in a patient in need thereof.

Certain embodiments are directed to methods of inducing net cell death over proliferation in a breast of a patient in need thereof.

Certain embodiments are directed to methods of inducing net extracellular matrix degradation over development of extracellular matrix in a breast of a patient in need thereof.

Certain embodiments are directed to methods of reversing cell number and mammographic breast density in a breast of a peri-menopausal patient.

Certain embodiments are directed to methods of reducing mammographic breast density and peri-menopausal symptoms in a patient in need thereof.

Certain embodiments are directed to methods for reducing and/or treating mammographic breast density and/or breast stiffness in a patient in need thereof, wherein the method increases the visualization of the breast by mammography, digital mammography, magnetic resonance imaging (MRI), ultrasound, digital breast tomosynthesis (DBT), virtual touch tissue imaging quantification (VTIQ), or combinations thereof.

Certain embodiments are directed to methods for providing an individualized reduction and/or treatment of mammographic breast density and/or breast stiffness in a patient in need thereof, comprising (i) determining the patient's MBD, and/or breast stiffness; (ii) optionally, measuring the patient's free androgenic index and/or alterations in the patient's free androgenic index over a period of time of at least one month; (iii) determining adjusted doses of an androgenic agent and/or aromoatse inhibitor taking into account the patient's body weight, total body fat, MBD, age, and free androgenic index; and (iv) administering the adjusted dose to said patient. In certain embodiments, the measuring the patient's free androgenic index and/or alterations in the patient's free androgenic index over a period of time of at least one month, may include taking a blood sample and measuring the amount of free androgenic agent (or testosterone) in the patient's serum.

Certain embodiments are directed to methods for reducing and/or treating mammographic breast density and/or breast stiffness in a patient in need thereof, wherein the method increases sensitivity of breast imaging detections by mammography, digital mammography, magnetic resonance imaging (MRI), ultrasound, digital breast tomosynthesis (DBT), virtual touch tissue imaging quantification (VTIQ), or combinations thereof.

Certain embodiments are directed to methods for reducing and/or treating mammographic breast density and/or breast stiffness in a patient in need thereof, wherein the method increases detection of breast cancer develops in the patient.

The methods disclosed herein may be used to effect one or more of the following in a patient: reducing mammographic breast density; treating mammographic breast density; reducing breast stiffness; treating breast stiffness; reducing mammographic breast density in a patient having a breast with a mammographic breast density of 7.5% or greater; reducing mammographic breast density in a patient having a breast with a BIRADS score of 3 or 4 (or c or d); inducing breast involution in a patient; inducing net cell death over proliferation in a breast of a patient; inducing net extracellular matrix degradation over development of extracellular matrix in a breast of a patient; methods of reversing cell number and mammographic breast density in a breast of a peri-menopausal patient; and reducing mammographic breast density and peri-menopausal symptoms in a patient. These methods may be useful in premenopausal and/or perimenopausal woman. These methods may also be useful in post-menopausal woman.

For example, high breast density in peri-menopause woman is known as a risk for developing breast cancer. The dense tissue in peri-menopausal women is not consider normal and has pathological implications. This increase in breast density may be due to a lifelong exposure to high levels of estrogen and progesterone in the presence of a low testosterone environment. The present inventors have discovered, among other things, that premenopausal and/or perimenopausal woman who receive effective amounts of testosterone and effective amounts of an aromataese inhibitor (such as anastrozole) may show a reduction in breast density and/or breast stiffness. The present inventors have also discovered that premenopausal and/or perimenopausal woman who receive effective amounts of testosterone and effective amounts of an aromatase inhibitor (such as anastrozole) may show an induction of breast involution and/or net cell death over proliferation. The present inventors have also discovered that an effective amount of an aromataese inhibitor in the breast tissue may be used to stop the conversion of testosterone to estrogen and thus allow testosterone to invoke an involution of the breast cells.

One or more of the following advantages is found in one or more of the disclosed methods.
   A. Enhanced mammographic detection due to reduced breast density enabling the mammogram to visualize malignancy at an earlier and/or less aggressive stage.
   B. Reduce the risk of interval breast cancer, such as those that may occur between mammographic screening rounds. These cancers are common in breasts with high MBD.
   C. Reduction in breast stiffness.
   D. Reduced pain during breast compression.
   E. Better compression is able to be achieved due at at least in part due to reduced pain.
   F. Because better compression is achieved and that the breast tissue is less dense the amount of energy required to expose the image on the mammogram is therefore reduced thus reducing the radiation of the breast tissue.

There are a number of categories used by diagnosticians and physicians to characterize the type and/or degree of mammographic breast density of a breast of a patient.

A diagnosing or treating physician may use one or more exams/tests to evaluate, characterize, and/or diagnose, a breast density, including but not limited to, mammography, digital mammography, magnetic resonance imagery (MRI), ultrasound, digital breast tomosynthesis (DBT), virtual touch tissue imaging quantification (VTIQ), or combinations thereof. The physician may also use other indicia, such as medical history or family history (to account for a genetic predispositon to breast density), and/or qualitative assessments of MBD, such as BIRADS (e.g., $5^{11}$ edition, using Breast Composition categories of "a" (the breasts are almost entirely fatty), "b" (there are scattered areas of fibroglandular density), "c" (the breasts are heterogeneously dense, which may obscure small masses), and "d" (the breasts are extremely dense, which lowers the sensitivity of mammography) (D'Orsi C J, Sickles E A, Mendelson E B, Morris E A et al. (2013). *ACR BI-RADS® Atlas, Breast Imaging Reporting and Data System*. Reston, Va.: American College of Radiology).

The androgenic agent may, for example, be selected from the group consisting of: testosterone, methyl testosterone, testosterone undecanoate, testosterone propionatedihydrotestosterone, 5α-dihydrotestosterone, or alternatively androstenediol androstenediol-3-acetate, androstenediol-17-acetate, androstenediol-3,17-diacetate, androstenediol-17-benzoate, androstenediol-3-acetate-17-benzoate, androstenedione, adrenosterone, androsterone acetate, androsterone propionate, androsterone benzoate, dehydroepiandrosterone, sodium dehydroepiandrosterone sulfate, oxymetholone, fluoxymesterone, methandrostenolone, testolactone, pregnenolone, 17α-methylnortestosterone, norethandrolone, dromostanolone, dromostanolone propionate, nandrolone, nandrolone phenpropionate, nandrolone decanoate, nandrolone furylpropionate, nandrolone cyclohexanepropionate, nandrolone benzoate, nandrolone cyclohexanecarboxylate, danazol, oxymetholone, androsterone, stanozolol, ethylestrenol, oxandrolone, bolasterone, mesterolone, testosterone cypionate, testosterone phenylacetate, testosterone enanthate, testosterone acetate, testosterone buciclate, testosterone heptanoate, testosterone decanoate, testosterone caprate, testosterone isocaprate, and isomers, metabolites, derivatives, precursors of the aforementioned compounds, or combinations thereof. In addition to the pharmaceutically acceptable esters of testosterone, esters of dihydrotestosterone, include, but are not limited to, the enanthate, propionate, cypionate, phenylacetate, acetate, isobutyrate, buciclate, heptanoate, decanoate, undecanoate, caprate and/or isocaprate esters.

The androgenic agent may, for example, be a selective androgenic receptor modulator ("SARM") and may comprise (2S)-3-(4-cyanophenoxy)-N-[4-cyano-3-(trifluoromethyl)phenyl]-2-hydroxy-2-methylpropanamide (also known as Enobosarm, Ostarine, GTx-024, and MK-2866), (7R,7aS)-2-Chloro-4-(7-hydroxy-1,3-dioxotetrahydropyrrolo[1,2-c]imidazol-2-yl)-3-methylbenzonitrile (also known as BMS-564,929), 4-((R)-2-((R)-2,2,2-trifluoro-1-hydroxyethyl)pyrrolidin-1-yl)-2-trifluoromethyl)benzonitrile (also known as LGD-4033, or Ligandrol), 4-(3-Hydroxy-8-aza-bicyclo[3.2.1]octyl)-naphthalene-1-carbonitrile (also known as AC-262,356), JNJ-28330835, 6-(bis-(2,2,2-trifluoroethyl)amino)-4-trifluoromethyl-1H-quinolin-2-one (also known as LGD-2226), 9-chloro-2-ethyl-1-methyl-3-(2,2,2-trifluoroethyl)-3H-pyrrolo[3,2-f]quinolin-7(6H)-one (also known as LGD-3303), 2-[4-(dimethylamino)-6-nitro-1,2,3,4-tetrahydroquinolin-2-yl]-2-methylpropan-1-ol (also known as S-40503), or (2S)—N-(4-cyano-3-trifluoromethylphenyl)-3-(3-fluoro-4-chlorophenoxy)-2-hydroxy-2-methyl-propanamide (also known as S-23), or derivatives thereof.

The androgenic agent may be selected from the group consisting of testosterone, methyltestosterone, testosterone undecanoate, testosterone propionate, a selective androgenic receptor modulator or combinations thereof.

The androgenic agents may be selected from the group consisting of naturally occurring androgens, synthetic androgens, selective androgenic receptor modulators, metabolites, precursors, derivatives thereof or combinations thereof. The agents may be incorporated into the present dosage units and thus administered in the form of a pharmaceutically acceptable derivative, metabolite, precursor, analog, ester, salt, or amide, or the agents may be modified by appending one or more appropriate functionalities to enhance selected biological properties such as penetration through mucosal tissue. In general, with regard to androgenic agents, the use of esters is desirable.

Preparation of esters, as noted in herein, involves functionalization of hydroxyl and/or carboxyl groups that may be present, as will be appreciated by those skilled in the arts of pharmaceutical chemistry and drug delivery. For example, to prepare testosterone esters, the 17-hydroxyl group of the testosterone molecule is generally caused to react with a suitable organic acid under esterifying conditions, such conditions typically involving the use of a strong acid such as sulfuric acid, hydrochloric acid, or the like, and a temperature sufficient to allow the reaction to proceed at reflux. Esters can be reconverted to the free acids, if desired, by using conventional hydrogenolysis or hydrolysis procedures.

The androgenic agent may be, for example, testosterone, methyltestosterone, testosterone undecanoate, testosterone propionate, dehydroepiandrosterone, or sodium dehydroepiandrosterone sulfate, or a metabolic precursor, metabolite, or derivative thereof. In certain embodiments, the androgenic agent may be provided in the form of testosterone undecanoate, an orally active testosterone preparation that is a fatty acid ester of the natural androgen testosterone. Unlike other oral testosterone preparations, testosterone undecanoate is able to by-pass the liver via the lymphatic system and is therefore orally bioavailable. In certain embodiments, the androgenic agent may be a SARM.

Additionally, testosterone is difficult to deliver orally, as 80-90% is broken down in the liver as it is absorbed from the gut. As such, alternate delivery mechanisms have been explored, e.g. the testosterone patch (Intrinsa®) by Proctor & Gamble used to improve sexual libido in post-menopausal women.

An effective amount of an androgenic agent may vary among androgenic agents. In addition, the effective amount per day of testosterone may also vary. In certain aspects, an effective amount of testosterone may be delivered by a buccal system, in the form of a 1 wt. % gel, in the form of a subcutaneous implant, in the form of an injection, in the form of a transdermal system, or by intramuscular administration. In certain embodiments, an effective amount of testosterone may be between 2 to 300 mg, such as, between 2 to 250 mg, between 2 to 200 mg, between 2 to 150 mg, between 2 to 100 mg, between 2 to 90 mg, between 200 to 300 mg, between 150 to 250 mg, between 100 to 200 mg, between 50 to 150 mg, between 40 to 120 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg or between 35 to 45 mg. For example, in certain embodiments, the effective amount of testosterone may be between 40 to 120 mg, for example, about 20 mg, about 40 mg, about 60 mg about 80 mg, about 100 mg or about 120 mg.

In certain embodiments, an effective amount of testosterone may be delivered by a buccal system, and may be between 2 to 100 mg, such as between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg.

In certain embodiments, an effective amount of testosterone may be delivered in the form of a 1 wt. % gel containing be between 2 to 100 mg testosterone, such as between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg testosterone.

In certain embodiments, an effective amount of testosterone may be delivered in the form of a subcutaneous implant, such as a subcutaneous pellet, containing between 2 to 200 mg testosterone, such as between 2 to 150 mg, between 2 to 100 mg, between 100 to 200 mg, between 50 to 150 mg, between 50 to 100 mg, between 40 to 100 mg, between 30 to 80 mg, between 2 to 90 mg, between 5 to 90 mg, between 5 to 80 mg, between 10 to 70 mg, between 20 to 60 mg, between 30 to 50 mg, between 2 to 50 mg, between 40 to 100 mg, between 60 to 100 mg, between 25 to 75 mg or between 35 to 45 mg testosterone.

In certain embodiments, an effective amount of testosterone may be delivered in the form of an injection, such as an injection of an aqueous suspension containing a concentration of testosterone of between 10 mg/mL to 150 mg/mL, such as between 20 mg/mL to 130 mg/mL, between 50 mg/mL to 125 mg/mL, between 75 mg/mL to 110 mg/mL, between 90 mg/mL to 150 mg/mL, between 100 mg/mL to 150 mg/mL, between 50 mg/mL to 100 mg/mL or between 10 mg/mL to 50 mg/mL.

In certain embodiments, an effective amount of testosterone may be delivered in the form of a transdermal system providing testosterone at a rate of between 0.1-10 mg/24 hours, such as at a rate of between 0.1-8 mg/24 hours, between 0.1-6 mg/24 hours, between 0.1-5 mg/24 hours, between 0.15-10 mg/24 hours, between 0.3-10 mg/24 hours, between 0.5-10 mg/24 hours, between 0.6-10 mg/24 hours, between 0.8-10 mg/24 hours, between 1-10 mg/24 hours, between 0.5-7.5 mg/24 hours, between 0.4-7 mg/24 hours, between 2-8 mg/24 hours, between 1.5-6 mg/24 hours, between 0.25-6 mg/24 hours, between 3-7 mg/24 hours, between 4-10 mg/24 hours, between 5-10 mg/24 hours or between 1-5 mg/24 hours.

In certain embodiments, an effective amount of testosterone may be by intramuscular administration, for example between about 5 to about 25 mg of testosterone at a rate of once every 2-3 weeks, or once every 2-4 weeks.

An effective amount per day of methyltestosterone may vary. In exemplary embodiments, the effective amount of methyltestosterone may be between 0.1 mg to 10 mg, such as between 0.5 mg to 9 mg, between 2 mg to 8 mg, between 3 mg to 7 mg, or between 4 mg to 5 mg. For example, the effective amount of methyltestosterone may be about 0.5 mg, about 1.25 mg or about 2.5 mg.

An effective amount per day of testosterone undecanoate may vary. In exemplary embodiments, the effective amount of testosterone undecanoate may be between 10 to 120 mg, such as between 20 to 110 mg, between 30 to 100 mg, between 40 to 90 mg, between 50 to 80 mg or between 60 to 70 mg. For example, the effective amount of testosterone undecanoate may be about 20 mg, about 40 mg or about 80 mg.

An effective amount per day of testosterone propionate may vary. In certain embodiments, the effective amount of testosterone propionate may be between 10 to 120 mg, such as between 20 to 110 mg, between 30 to 100 mg, between 40 to 90 mg, between 50 to 80 mg or between 60 to 70 mg. For example, the effective amount of testosterone propionate may be about 20 mg, about 40 mg or about 80 mg.

An effective amount per day of testosterone cypionate may vary. In certain embodiments, an effective amount of testosterone cypionate may be delivered by a buccal system, in the form of a 1 wt. % gel, a subcutaneous implant, an injection, a transdermal system, by intramuscular administration or combinations thereof. In certain embodiments, the effective amount of testosterone cypionate may be between 2 to 450 mg, such as between 2 to 400 mg, between 2 to 350 mg, between 2 to 300 mg, between 2 to 250 mg, between 2 to 200 mg, between 2 to 150 mg, between 2 to 100 mg, between 2 to 90 mg, between 200 to 450 mg, between 200 to 400 mg, between 350 to 450 mg, between 300 to 400 mg, between 200 to 300 mg, between 150 to 250 mg, between 100 to 200 mg, between 50 to 150 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg or between 35 to 45 mg.

For example, an effective amount of testosterone cypionate may be delivered in the form of an injection, such as an injection of an aqueous suspension containing a concentration of testosterone cypionate of between 2 mg/mL to 200 mg/mL, such as between 2 mg/mL to 150 mg/mL, between 2 mg/mL to 100 mg/mL, between 5 mg/mL to 200 mg/mL, between 5 mg/mL to 150 mg/mL, between 10 mg/mL to 150 mg/mL, between 20 mg/mL to 130 mg/mL, between 50 mg/mL to 125 mg/mL, between 75 mg/mL to 110 mg/mL, between 90 mg/mL to 150 mg/mL, between 100 mg/mL to 150 mg/mL, between 50 mg/mL to 100 mg/mL, between 100 mg/mL to 200 mg/mL, between 150 mg/mL to 200 mg/mL, between 75 mg/mL to 150 mg/mL, between 125 mg/mL to 175 mg/mL or between 10 mg/mL to 50 mg/mL.

In certain embodiments, an effective amount of testosterone cypionate may be by intramuscular administration, for example between 5 to 25 mg of testosterone cypionate at a rate of once every 2-3 weeks, or once every 2-4 weeks.

An effective amount per day of testosterone enanthate may vary. In certain embodiments, an effective amount of testosterone enanthate may be delivered by a buccal system, in the form of a 1 wt. % gel, a subcutaneous implant, an injection, a transdermal system, by intramuscular administration or combinations thereof. In certain embodiments, the effective amount of testosterone enanthate may be between 2 to 500 mg, such as between 2 to 400 mg, between 200 to 500 mg, between 200 to 400 mg, between 200 to 350 mg, between 300 to 500 mg, between 350 to 450 mg, between 400 to 500 mg, between 2 to 275 mg, between 2 to 225 mg, between 2 to 175 mg, between 2 to 125 mg, between 2 to 90 mg, between 200 to 300 mg, between 150 to 250 mg, between 100 to 200 mg, between 50 to 450 mg, between 50 to 350 mg, between 50 to 200 mg, between 50 to 100 mg, between 100 to 300 mg, between 40 to 100 mg, between 30 to 80 mg, between 5 to 75 mg, between 10 to 70 mg, between 20 to 60 mg, between 30 to 50 mg, or between 35 to 45 mg.

In certain embodiments, an effective amount of testosterone enanthate may be delivered by a buccal system, and may be between 2 to 100 mg for 1-3 times per day, such as between 5 to 80 mg, between 10 to 70 mg, between 20 to 60 mg, between 30 to 50 mg, between 60 to 100 mg, between 25 to 75 mg, between 25 to 35 mg, between 20 to 30 mg, or between 35 to 45 mg for 1-3 times per day.

In certain embodiments, an effective amount of testosterone enanthate may be delivered in the form of a subcutaneous implant, such as a subcutaneous pellet, containing between 2 to 500 mg testosterone enanthate, such as between 2 to 400 mg, between 200 to 500 mg, between 200 to 400 mg, between about 200 to about 350 mg, between 300 to 500 mg, between 2 to 250 mg, between 2 to 200 mg, between 2 to 150 mg, between 2 to 100 mg, between 200 to 300 mg, between 150 to 250 mg, between 50 to 400 mg, between 50 to 300 mg, between 50 to 150 mg, between 50 to 100 mg, between 40 to 100 mg, between 30 to 80 mg, between 10 to 70 mg, between 30 to 50 mg or between 35 to 45 mg testosterone enanthate.

In certain embodiments, an effective amount of testosterone enanthate may be delivered in the form of an injection, such as an injection of an oil formulation containing a concentration of testosterone enanthate of between 2 mg/mL to 250 mg/mL, such as between 2 mg/mL to 200 mg/mL, between 150 mg/mL to 200 mg/mL, between 150 mg/mL to 250 mg/mL, between 10 mg/mL to 150 mg/mL, between 50 mg/mL to 125 mg/mL, between 75 mg/mL to 110 mg/mL, between 90 mg/mL to 150 mg/mL, between 50 mg/mL to 100 mg/mL or between 10 mg/mL to 50 mg/mL.

In certain aspects, an effective amount of testosterone enanthate may be delivered in the form of a transdermal system providing testosterone enanthate at a rate of between 0.1-10 mg/24 hours, such as at a rate of between 0.1-8 mg/24 hours, between 0.1-6 mg/24 hours, between 0.1-5 mg/24 hours, between 0.2-10 mg/24 hours, between 0.4-10 mg/24 hours, between 0.5-10 mg/24 hours, between 0.7-10 mg/24 hours, between 0.8-10 mg/24 hours, between 1-10 mg/24 hours, between 0.5-7.5 mg/24 hours, between 1.5-6 mg/24 hours, between 0.25-6 mg/24 hours, between 3-7 mg/24 hours, between 4-10 mg/24 hours, between 5-10 mg/24 hours or at a rate of between 1-5 mg/24 hours.

In certain embodiments, an effective amount of testosterone enanthate may be by intramuscular administration, for example, between 50 to 400 mg of testosterone enanthate at a rate of once every 2-3 weeks, or once every 2-4 weeks, for example, between 60 to 200 mg of testosterone enanthate at a rate of once every 2-3 weeks, or once every 2-4 weeks.

An effective amount per day of a SARM may vary. In certain embodiments, an effective amount of the selective androgenic receptor modulator may be between 10 to 120 mg, between 30 to 100 mg, between 50 to 80 mg or between 60 to 70 mg. For example, in certain aspects, the effective amount of the selective androgenic receptor modulator may be about 20 mg, about 40 mg, or about 80 mg.

The effective amount of androgenic agent used in conjunction with an aromatase inhibitor may be relatively lower than a standard dose because of low levels of sex hormone binding globulin which may be caused by the aromatase inhibitor.

Sex hormone binding globulin binds an androgenic agent (e.g., testosterone) and transports it around the body. Its production is regulated by several mechanisms, but one of the effectors of its level is the amount of estrogen in the serum: the higher the estrogen, the higher the sex hormone binding globulin and the lower the free androgenic agent. Conversely, the lower the estrogen, the lower the sex hormone binding globulin, and the higher the free androgenic agent, which means the androgenic agent has higher bioavailability. Thus after menopause, as the estrogen level falls, the sex hormone binding globulin level falls and the free androgenic agent such as testosterone rises. This free androgenic agent has multiple functions, as the androgen receptor is expressed in all cells of the body.

In certain embodiments, the dosage levels below the lower limit of the aforesaid range of the androgenic agent may be more than adequate, while in other cases still larger doses above the upper limit of the aforesaid range may be employed without causing any harmful side effects.

In certain embodiments, the aromatase inhibitor may be, for example, a steroidal aromatase inhibitor, a nonsteroidal aromatase inhibitor, and/or isomers thereof. Steroidal aromatase inhibitors developed to date build upon the basic androstenedione nucleus and incorporate chemical substituents at varying positions on the steroid. Examples of steroidal aromatase inhibitors include, but are not limited to, exemestane (Aromasin®) and formestane. Additional examples include mechanism-based steroidal aromatase inhibitors that mimic the substrate, are converted by the enzyme to a reactive intermediate, and result in the inactivation of aromatase. In certain embodiments, the aromatase inhibitor is exemestane. Nonsteroidal aromatase inhibitors may be divided into three classes: aminoglutethimide-like molecules, imidazole/triazole derivatives, and flavonoid analogs. Examples of nonsteroidal aromatase inhibitors include, but are not limited to, anastrozole (Arimidex®), letrozole (Femara®), vorozole and fadrozole. In certain embodiments, the aromatase inhibitor is either anastrozole or letrozole. In certain embodiments, the aromatase inhibitor is anastrozole.

Aromatase inhibitors often include third-generation aromatase inhibitors, such as anastrozole (Arimidex®), exemestane (Aromasin®), and letrozole (Femara®). These third generation aromatase inhibitors have brought a change in the therapeutic approach to patients with hormone-sensitive breast cancer. Such aromatase inhibitors are specific in their action in that they virtually ablate estrogen in the serum and thus lower sex hormone binding globulin, which enables the achievement of a synergistic effect.

In certain embodiments, the aromatase inhibitor may be selected from the group consisting of anastrozole, exemestane, or letrozole. In certain embodiments, the aromatase inhibitor is either anastrozole or letrozole. In certain embodiments, the aromatase inhibitor is anastrozole.

The effective amount of an aromatase inhibitor may vary among aromatase inhibitors. In certain embodiments, an effective amount of an aromatase inhibitor may be delivered orally, in the form of a subcutaneous implant or a transdermal system or combinations thereof. The effective amount per day for anastrozole (Aromasin®) may vary. For example, the effective amount of Aromasin® may be between 0.1 to 150 mg, such as between 0.1 to 50 mg, between 0.1 to 10 mg, between 0.1 to 8 mg, between 0.1 to 6 mg, between 0.1 to 5 mg, between 0.1 to 4 mg, between 0.1 to 2 mg, between 0.1 to 1 mg, between 0.5 to 5 mg, between 1 to 10 mg, between 5 to 100 mg, between 10 to 80 mg, between 25 to 150 mg, between 30 to 60 mg, between 80 to 150 mg, or between 40 to 50 mg. For example, in certain aspects, the effective amount of Aromasin® may be about 25 mg, about 10 mg, about 5 mg, about 3 mg, about 2 mg, about 1 mg or about 0.5 mg.

The effective amount per day of Arimidex® may vary. For example, the effective amount for exemestane (Arimidex®) may be between 0.1 mg to 200 mg, such as between 5 mg to 200 mg, between 20 mg to 200 mg, between 50 mg to 200 mg, between 80 mg to 200 mg, between 100 mg to 200 mg, between 150 mg to 200 mg, between 1 mg to 100 mg, between 50 mg to 100 mg, between 80 mg to 100 mg, between 50 mg to 80 mg, between 0.1 mg to 20 mg, between 0.1 mg to 10 mg, between 0.1 mg to 5 mg, between 0.5 mg to 1.5 mg, between 1.5 mg to 2.5 mg, between 1.5 mg to 5 mg, between 1 mg to 7.5 mg, or between 1 mg to 20 mg. For example, in certain embodiments, the effective amount for exemestane (Arimidex®) may be about 1 mg. In certain embodiments, the effective amount for exemestane (Arimidex®) may be about 100 mg, about 80 mg or about 60 mg.

The effective amount per day of Femara® may vary. For example, the effective amount of letrozole (Femara®) may be between 0.1 mg to 20 mg, such as between 0.1 mg to 10 mg, between 5 mg to 15 mg, between 1 mg to 5 mg, between 2.5 mg to 3 mg, between 2.5 mg to 5 mg, between 2.5 mg to 7.5 mg or between 2.5 mg to 10 mg. In certain embodiments, the effective amount of letrozole (Femara®) may be about 5 mg, about 2.5 mg or about 1 mg.

In certain embodiments, a method is provided for determining if the patient has a breast with a BIRADS score of 3 or 4 (or c or d); a breast with a mammographic breast density of 7.5% or greater; a mammographically dense breast; a breast with the same or more breast tissue than fat; a breast with more breast tissue than fat; breast cancer or combinations thereof.

In certain embodiments, the patient has, or is diagnosed with having, a breast with a BIRADS score (1-4 scale) in the range of between 2 and 4, for example between 2 and 3, or between 3 and 4. In certain embodiments, the patient has, or is diagnosed with having, a breast with a BIRADS score of 2 or more, for example, a BIRADS score of 3 or 4, or a BIRADS score of 4.

In certain embodiments, the patient has, or is diagnosed with having, a breast with a BIRADS score (a-d scale) in the range of between b and d, for example between b and c, or between c and d. In certain embodiments, the patient has, or is diagnosed with having, a breast with a BIRADS score of b or more, for example, a BIRADS score of c or d, or a BIRADS score of d.

In certain embodiments, the patient has, or is diagnosed with having, a breast with a mammographic breast density of 7.5% or greater, for example, a mammographic breast density of 10% or greater, 15% or greater, 20% or greater, 30% or greater, 50% or greater, 70% or greater, or 95% or greater.

In certain embodiments, the patient has, or is diagnosed with having, a breast with a BIRADS score of 3 (or c) and a mammographic breast density of 7.5% or greater, for example, a mammographic breast density of 10% or greater, 15% or greater, 20% or greater, 30% or greater, 50% or greater, 70% or greater, or 95% or greater. In certain embodiments, the patient has, or is diagnosed with having, a breast with a BIRADS score of 4 (or d) and a mammographic breast density of 7.5% or greater, for example, a mammographic breast density of 10% or greater, 15% or greater, 20% or greater, 30% or greater, 50% or greater, or greater, or 95% or greater. In certain embodiments, the patient has, or is diagnosed with having, a breast with a mammographic breast density in the range of between 1% to 100%, for example, a mammographic breast density of between 1% and 24%, between 5% to 100%, between 5% to 95%, between 5% to 90%, between 5% to 80%, between 5% to 70%, between 5% to 60%, between 5% to 50%, between 5% to 40%, between 5% to 30%, between 5% to 25%, between 5% to 20%, between 10% to 100%, between 10% to 95%, between 10% to 90%, between 10% to 80%, between 10% to 70%, between 10% to 60%, between 10% to 50%, between 10% to 40%, between 10% to 30%, between 10% to 25%, between 10% to 20%, between 25% to 100%, between 25% to 75%, between 25% to 50%, between 25% to 49%, between 30% to 100%, between 30% to 95%, between 30% to 90%, between 30% to 80%, between 30% to 70%, between 30% to 60%, between 30% to 50%, between 30% to 40%, between 40% to 100%, between 40% to 95%, between 40% to 90%, between 40% to 80%, between 40% to 70%, between 40% to 60%, between 40% to 50%, between 50% to 100%, between 50% to 95%, between 50% to 90%, between 50% to 80%, between 50% to 75%, between 50% to 74%, between 50% to 70%, between 50% to 60%, between 75% to 100%, between 75% to 95%, or a mammographic breast density of between 75% to 90%.

In certain embodiments, the patient has, or is diagnosed with having, a mammographically dense breast, for example, a breast having about the same or more breast tissue than fat.

In certain embodiments, the patient is a perimenopausal woman or a postmenopausal woman. In certain embodiments, the patient is a perimenopausal woman.

In certain embodiments, the duration of treatment for administration of an androgenic agent, an aromatase inhibitor, or a pharmaceutical composition a combination of the same, may vary between about 1 week to about 20 years, for example, between about 1 month to about 20 years, between about 3 months to about 10 years, between about 4 months to about 5 years, and between about 6 months to about 4 years. In certain embodiments, the duration of treatment may be about 3 months, 6 months, about 9 months, about 1 year, 1.5 years, 2 years, 2.5 years, 3 years, 3.5 years, 4 years, 4.5 years, 5 years, 5.5 years, 6 years, 7 years, 10 years, 13 years, 15 years, or 20 years.

In certain embodiments, the method reduces or decreases the patient's BIRADS score between one or more annual intervening mammographic detections. For example, the method reduces or decreases the patient's BIRADS score by 1 or more points between one or more annual intervening mammographic detections, such as, by 2 or more, 3 or 4, or 4 points between one or more annual intervening mammographic detections. In certain embodiments, the method reduces or decreases the patient's BIRADS score by 1 point between one or more annual intervening mammographic detections, for example, by 2, 3, or 4 points between one or more annual intervening mammographic detections. In certain embodiments, the method maintains or stabilizes the patient's BIRADS score between one or more annual intervening mammographic detections.

The time period between the one or more annual intervening mammographic detections may be 1 to 20 years, for example, 1 year, 1.5 years, 2 years, 3 years, 4 years, 5 years, 6 years, 10 years, 15 years, or 20 years. The time period between the one or more annual intervening mammographic detections may be 1 year, 2 years, 4 years, 5 years, 7 years, 10 years, 15 years, or 20 years.

In certain embodiments, the method reduces or decreases the mammographic breast density of the patient's breast between one or more annual intervening mammographic detections. For example, the method reduces or decreases the mammographic breast density of the patient's breast in the range of between 1% to 99% between one or more annual intervening mammographic detections, such as, in the range of between 1% to 80%, between 1% to 50%, between 1% to 30%, between 1% to 20%, between 1% to 10%, between 3% to 40%, between 3% to 20%, between 5% to 60%, between 5% to 25%, between 5% to 15%, between 5% to 10%, between 10% to 60%, between 10% to 40%, between 10% to 30%, between 10% to 20%, between 10% to 15%, between 20% to 60%, between 20% to 40%, between 20% to 30%, between 30% to 60%, between 30% to 50%, or between 30% to 40% between one or more annual intervening mammographic detections. For example, the method reduces or decreases the mammographic breast density of the patient's breast by at least 2% between one or more annual intervening mammographic detections, such as, by at least 5%, 10%, 20%, 30%, 40%, 50%, 75%, 85%, 95%, or 99% between one or more annual intervening mammographic detections. In certain embodiments, the method maintains or stabilizes the mammographic breast density of the patient's breast between one or more annual intervening mammographic detections.

In certain embodiments, the method reduces or decreases the mammographic breast density of the patient's breast by at least 2%, such as 5%, 10%, 20%, or 30%, over a 4 hour period, such as over an 8 hour, 24 hour, 1 day, 3 days, 1 week, 2 weeks, 1 month, 2 month, 3 months, 6 months, 9 months, or 1 year period.

In certain embodiments, the method mitigates or reduces the patient's risk of developing breast cancer. For example, in certain embodiments, the method mitigates, reduces or the patient's risk of developing breast cancer between one or more annual intervening mammographic detections. In certain embodiments, the method mitigates, reduces or the patient's risk of developing breast cancer and avoids, mitigates, reduces or reverses one or more peri-menopausal symptoms between one or more annual intervening mammographic detections. For example, the one or more peri-menopausal symptoms that may be mitigated, reduced, or avoided may include, but is not limited to, menstrual irregularity; hot flashes and sleep problems; mood changes; mood swings; irritability; depression; vaginal dryness; urinary or vaginal infections; urinary incontinence; decreasing fertility; changes in sexual arousal or desire; bone loss; fragile bones; osteoporosis; or changing cholesterol levels, such as an increase in low-density lipoprotein (LDL) cholesterol, a decrease in high-density lipoprotein (HDL) cholesterol; or combinations thereof.

In certain embodiments, the method increases or improves the patient's fat to breast tissue ratio between one or more annual intervening mammographic detections. For example, the method increases or improves the patient's fat to breast tissue ratio from 1:19 to 19:1 between one or more annual intervening mammographic detections, such as increases or improves the treated patient's fat to breast tissue ratio from 1:15 to 19:1, from 1:10 to 19:1, from 1:5 to 19:1, from 1:2 to 19:1, from 2:3 to 19:1, from 2:1 to 19:1, from 4:1 to 19:1, from 6:1 to 19:1, from 8:1 to 19:1, from 10:1 to 19:1, from 1:19 to 10:1, from 1:10 to 10:1, from 1:4 to 10:1, from 1:2 to 10:1, from 3:2 to 10:1, from 3:1 to 10:1, from 5:1 to 10:1, from 7:1 to 10:1, from 9:1 to 10:1, from 15:1 to 10:1, from 1:15 to 5:1, from 1:5 to 5:1, from 1:3 to 5:1, from 3:2 to 5:1, from 3:1 to 5:1, from 6:1 to 5:1, 8:1 to 5:1, from 10:1 to 5:1, from 1:19 to 3:1, from 1:10 to 3:1, from 1:4 to 3:1, from 1:2 to 3:1, from 2:1 to 3:1, from 4:1 to 3:1, from 6:1 to 3:1, from 8:1 to 3:1, from 10:1 to 3:1, or from 15:1 to 3:1 between one or more annual intervening mammographic detections.

In certain embodiments, the method increases or improves the patient's fat to breast tissue ratio from 1:19 to 19:1, such as from 1:10 to 19:1, from 1:5 to 19:1, from 1:2 to 19:1, from 2:3 to 19:1, from 2:1 to 19:1, over a 4 hour period, over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the method increases the percentage of fat in the treated patient's breast between one or more annual intervening mammographic detections. For example, the method increases the percentage of fat in the treated patient's breast in the range of between 1% to 99% between one or more annual intervening mammographic detections, such as, in the range of between 1% to 90%, between 1% to 70%, between 1% to 50%, between 1% to 30%, between 1% to 20%, between 1% to 15%, between 1% to 10%, between 3% to 60%, between 3% to 20%, between 5% to 70%, between 5% to 50%, between 5% to 30%, between 5% to 20%, between 5% to 15%, between 5% to 10%, between 10% to 60%, between 10% to 40%, between 10% to 30%, between 10% to 20%, between 10% to 15%, between 20% to 50%, between 20% to 30%, between 30% to 60%, between 30% to 50%, or between 30% to 40% between one or more annual intervening mammographic detections.

In certain embodiments, the method increases the percentage of fat in the treated patient's breast by at least 2%, such as by at least 5%, by at least 10%, by at least 25%, by at least 40%, by at least 75%, by at least 95%, or by at least 99%, over a 4 hour period, such as over an 8 hour period, over a 24 hour period, over a 3 day period, over a 1 week period, over a 2 week period, over a 1 month period, over a 2 month period, over a 3 month period, over a 6 month period, over a 9 month period, over a 1 year period, or over a 5 year period.

In certain embodiments, the method enhances, increases, or improves, breast compression during mammographic visualization or detection of the breast between one or more annual intervening mammographic detections. For example, the method enhances, increases, or improves, breast compression during mammographic visualization or detection of the breast in the range of between 5% to 70%, between 5% to 50%, between 5% to 30%, between 5% to 20%, between 5% to 15%, between 5% to 10%, between 10% to 50%, between 10% to 30%, between 10% to 20%, between 10% to 15%, between 20% to 60%, between 20% to 40%, between 20% to 30%, between 30% to 70%, between 30% to 50%, or between 30% to 40% between one or more annual intervening mammographic detections. In certain embodiments, as a result of the enhanced, increased, or improved, breast compression during mammographic visualization or detection of the breast, the method further mitigates or reduces the patient's pain during the breast compression. For example, the method further mitigates, reduces or minimizes, the patient's pain during the breast compression in the range of between 5% to 80%, between 5% to 50%, between 5% to 30%, between 5% to 20%, between 5% to 15%, between 5% to 10%, between 10% to 80%, between 10% to 60%, between 10% to 40%, between 10% to 20%, between 10% to 15%, between 20% to 70%, between 20% to 50%, between 20% to 30%, between 30% to 70%, between 30% to 50%, or between 30% to 40% less pain as a result of the enhanced, increased, or improved, breast compression during mammographic visualization or detection of the breast.

In certain embodiments, the method mitigates or reduces the patient's pain during the breast compression. For example, the method mitigates or reduces the patient's pain during the breast compression in the range of between 5% to 80%, between 5% to 60%, between 5% to 30%, between 5% to 20%, between 5% to 15%, between 5% to 10%, between 10% to 80%, between 10% to 60%, between 10% to 40%, between 10% to 30%, between 10% to 20%, between 10% to 15%, between 20% to 70%, between 20% to 50%, between 20% to 30%, between 30% to 90%, between 30% to 50%, or between 30% to 40% between one or more annual intervening mammographic detections. In certain embodiments, as a result of the patient's mitigated, reduced or minimized pain during the breast compression, the method further enhances, increases, or improves, breast compression during mammographic visualization or detection of the breast between one or more annual intervening mammographic detections. For example, the method further enhances, increases, or improves, breast compression during mammographic visualization or detection of the breast between one or more annual intervening mammographic detections in the range of between 5% to 80%, between 5% to 60%, between 5% to 40%, between 5% to 30%, between 5% to 20%, between 5% to 15%, between 5% to 10%, between 10% to 80%, between 10% to 60%, between 10% to 40%, between 10% to 20%, between 10% to 15%, between 20% to 80%, between 20% to 60%, between 20% to 30%, between 30% to 80%, between 30% to 50%, or between 30% to 40% between one or more annual intervening mammographic detections.

In certain embodiments, the method mitigates or reduces the patient's pain according to the visual analog scale (VAS) during the breast compression. For example, the method mitigates or reduces the patient's pain according to the VAS during the breast compression such that the patient does not suffer from significant pain between 50-100 mm, between 50-80 mm, between 50-70 mm, between 60-100 mm, between 70-100 mm, between 80-100 mm or between 90-100 mm during one or more mammographic detections or during one or more annual intervening mammographic detections.

In certain embodiments, the method enhances increases or improves the patient's compliance of having regular mammographic visualizations or detections, for example, compliance with mammographic visualizations or detections at every 6 months, annually, every 2 years, every 3 years, or every 5 years.

In certain embodiments, the method mitigates or reduces the amount of radiation exposure required to visualize or detect the patient's breast during one or more subsequent mammographies, such as during one or more subsequent annual mammographies. For example, the method mitigates or reduces the amount of radiation exposure required to visualize or detect the patient's breast in the range of between 5% to 99%, between 5% to 80%, between 5% to 70%, between 5% to 50%, between 5% to 30%, between 5% to 20%, between 5% to 15%, between 5% to 10%, between 10% to 80%, between 10% to 60%, between 10% to 40%, between 10% to 20%, between 10% to 15%, between 20% to 80%, between 20% to 60%, between 20% to 40%, between 20% to 30%, between 30% to 80%, between 30% to 60%, between 30% to 50% or between 30% to 40% during one or more subsequent mammographies, such as during one or more subsequent annual mammographies.

In certain embodiments, the method induces breast involution in the breast of the patient, for example in the breast of a peri-menopausal patient.

In certain embodiments, the method induces involution of breast cells in the breast of the patient, for example in the breast of a peri-menopausal patient.

In certain embodiments, the method induces net cell death over proliferation in the breast of the patient, for example in the breast of a peri-menopausal patient.

In certain embodiments, the method reverses cell number and mammographic breast density in the breast of the patient, for example in the breast of a peri-menopausal patient.

In certain embodiments, the method mitigates or reduces breast stiffness in the breast of the patient, for example in the breast of a peri-menopausal patient. For example, the method mitigates or reduces breast stiffness in the breast of the patient in the range of between 5% to 80%, between 5% to 60%, between 5% to 40%, between 5% to 20%, between 5% to 15%, between 5% to 10%, between 10% to 80%, between 10% to 60%, between 10% to 40%, between 10% to 30%, between 10% to 20%, between 10% to 15%, between 20% to 80%, between 20% to 60%, between 20% to 40%, between 20% to 30%, between 30% to 80%, between 30% to 60%, or between 30% to 40%, between one or more annual intervening mammographic detections. For example, the method mitigates or reduces breast stiffness in the breast of the patient by at least 5%, such as at least 8%, at least 10%, at least 15%, at least 20%, or at least 30%, per annum. In certain embodiments, the method mitigates or reduces breast stiffness in the breast of the patient by at least 5%, such as at least 8%, at least 10%, at least 15%, at least 20%, or at least 30%, over a 4 hour period, such as over an 8 hour period, a 24 hour period, a 3 day period, a 1 week period, a 2 week period, a 1 month period, a 2 month period, a 3 month period, a 6 month period, a 9 month period, a 1 year period, or a 5 year period.

In certain embodiments, the method enhances, increases, or improves mammographic visualization or detection of the breast of the patient, for example the breast of a peri-menopausal patient. For example, the method enhances, increases, or improves mammographic visualization or detection of the breast of the patient in the range of between 5% to 80%, between 5% to 50%, between 5% to 30%, between 5% to 20%, between 5% to 15%, between 5% to 10%, between 10% to 80%, between 10% to 60%, between 10% to 30%, between 10% to 20%, between 10% to 15%, between 20% to 80%, between 20% to 60%, between 20% to 30%, between 30% to 80%, between 30% to 60%, or between 30% to 40%, between one or more annual intervening mammographic detections. In certain embodiments, the method enhances, increases, or improves mammographic visualization or detection of the breast of the patient by at least 5%, such as at least 10%, at least 15%, at least 25%, at least 40%, at least 50%, or at least 75%, over a 4 hour period, or over other time periods, such 8 hours, 24 hours, 3 days, 1 week, 2 weeks, 1 month, 2 month, 3 months, 6 months, 9 months, 1 year, or 5 years.

In certain embodiments, the method reduces mammographic breast density and avoids inducing masculinizing androgenic side-effects or inducing a hyper-androgenic state. For example, masculinizing androgenic side-effects may include male-type baldness, hirsutism, or increased hair in areas unwanted by said patient, voice deepening, acne, or combinations thereof. In certain embodiments, the method reduces mammographic breast density and is exclusive of inducing masculinizing androgenic side-effects or inducing a hyper-androgenic state. In certain embodiments, the method reduces mammographic breast density and minimizes induction of masculinizing androgenic side-effects or induction of a hyper-androgenic state.

In certain embodiments, the method substantially improves or improves the patient's physical functioning, such as physical functioning related to the patient's central nervous system, libido, musculoskeletal system, cardiovascular system, risk of contracting autoimmune diseases, severity of symptoms associated with autoimmune disease, or combinations thereof. For example, as related to the patient's central nervous system, the method may reduce depression, anxiety, general cognitive dysfunction including memory, or reduce the risk of dementia and Parkinsonism. For example, as related to the patient's libido, the method may provide a significant improvement in global libido, including speed to sexual arousal and ability to achieve orgasm. For example, as related to the patient's musculoskeletal system, the method may provide for a reduction in inflammatory and degenerative arthritis, an improvement in bone mineral density, or an improvement in muscle strength. For example, as related to the patient's cardiovascular system, the method may provide a reduction in foamy macrophage deposition in the arterial wall, a reduction in atherosclerosis, an increase in high density lipoprotein's leading to an improvement in cholesterol, or a high density lipoprotein ratio. For example, as related to the patient's risk of contracting autoimmune diseases, the method may substantially reduces or reduces the treated patient's risk of contracting autoimmune diseases, such as Sjogren's syndrome, lupus, and rheumatoid arthritis. For example, as related to the severity of symptoms associated with the patient's autoimmune disease, the method may substantially reduces or reduces the severity of symptoms associated with a treated patient's autoimmune disease, such as Sjogren's syndrome, lupus, and rheumatoid arthritis. In certain embodiments, the method substantially improves or improves the patient's physical functioning, such as cognitive function; reduction of a degenerative CNS disease, comprising dementia or parkinsonism; muscle strength; libido; energy; reduction of monoamine oxidase induced anxiety and depression; or combinations thereof.

In certain embodiments, the method further provides one or more of the following: i) reduces mammographic breast density; ii) increases involutionary effects on the patient's breast without conversion of testosterone to estrogen; iii) substantially reduces, reduces, or reverses peri-menopausal symptoms; or iv) substantially improves or improves the patient's physical functioning, comprising cognitive function; reduction of a degenerative CNS disease, comprising dementia or parkinsonism; muscle strength; libido; energy;

reduction of monoamine oxidase induced anxiety and depression; or combinations thereof. In certain embodiments, the method further provides one or more of the following: i) reduces mammographic breast density; ii) increases involutionary effects on hormonally affected end organs, comprising breast, without conversion of testosterone to estrogen; iii) substantially reduces, reduces, or reverses peri-menopausal symptoms related to fluctuating estrogen levels; or iv) substantially improves or improves the patient's physical functioning, comprising cognitive function; reduction of a degenerative CNS disease, comprising dementia or parkinsonism; muscle strength; libido; energy; reduction of monoamine oxidase induced anxiety and depression; or combinations thereof.

In certain embodiments, the patient has a high free androgenic index level, for example 30% or greater, within their breast within four hours of the administration of the androgenic agent and the aromatase inhibitor. In certain embodiments, the patient has a supra-physiological free androgenic index level within their breast within four hours of the administration of the androgenic agent and the aromatase inhibitor.

In certain embodiments, the method further comprises: a) measuring free androgenic index levels and/or aromatase inhibitor levels in serum isolated from a blood sample taken from the patient after at least 1 month of treatment; b) determining a subsequent dose, comprising a subsequent effective amount of androgenic agent and a subsequent effective amount of an aromatase inhibitor; and c) administering to the patient the subsequent dose.

In certain embodiments, the method further comprises: a) measuring free androgenic index levels and/or aromatase inhibitor levels in serum isolated from a blood sample taken from the patient after at least 1 month of treatment, comprising centrifuging the patient's blood sample to isolate the serum; b) determining a subsequent dose, comprising a subsequent effective amount of androgenic agent and a subsequent effective amount of an aromatase inhibitor; and c) administering to the patient the subsequent dose.

In certain embodiments, the measured free androgenic index serum levels of a treated patient after 1 month may be between 10-25%, such as between 10-20%, between 10-15%, between 15-25%, between 15-20%, between 12-18%, between 8-15%, or between 11-14%.

In certain embodiments, the measured free androgenic index serum levels of a treated patient after 3 months may be between 2-10%, such as between 2-8%, between 2-6%, between 2-5%, between 2-4%, between 4-10%, between 5-8%, between 3-7%, between 4-6%, between 3-6%, between 4-7%, between 5-10% or between 2-5%.

In certain embodiments, the administration of the aromatase inhibitor reduces aromatization of testosterone to estrogen in the subcutaneous fat of the treated patient, for example reduces aromatization by 80-95%, or 100%. For example, the administered aromatase inhibitor may reduce aromatization of testosterone to estrogen in the subcutaneous fat of the patient's breast, the subcutaneous fat of the patient's pelvis, the subcutaneous fat of the patient's buttocks, the subcutaneous fat of the patient's abdomen or combinations thereof, for example reduces aromatization by 80-95%, or 100%.

In certain embodiments, the administration of the androgenic agent and the aromatase inhibitor is a co-administration. For example, the co-administration may be concurrently, simultaneously, substantially at the same time, or sequentially.

Dosing Algorithm

Certain embodiments involves the identification of women in the peri-menopause who have mammographically dense breast tissue, as described by an appropriate mathematical algorithm produced from pre-presentation mammographic images, who are then treated with T 1 mg to 200 mg combined with a third-generation Ai such as but not confined to anastrozole or letrozole (0.5-20 mg) and administered by subcutaneous application.

In certain embodiments, the anastrozole dose (AD) and the testosterone dose (TD), both measured in mg, are given as a function of the following formulas $$AD = F1(N, T, BW, TBF, MBD, BS, AGE, FAI(T), AI(T), TD) \quad \text{Formula 1}$$

$$TD = F2(N, T, BW, TBF, MBD, BS, AGE, SAL(T), AI(T)) \quad \text{Formula 2}$$

wherein:
N is the dose number (N=1 being the first dose);
T is time in months from the first dose;
BW is body weight measured in kg;
TBF is fraction of BW measured by bio-impedance;
MBD is mammographic breast density, being the percentage of breast fibro-glandular tissue relative to total breast volume where the MBD is the average of both breasts, e.g., measured by Volpara breast density software;
Age=years;
AI(T) is the Androgenicity Index as a function of time which is given by:

$$AI(T) = F3(H, A, VD, SHL) \quad \text{Formula 3}$$

wherein each of the parameters is measured at time T and
H is a measure of Hirutism;
A is a measure of Acne;
VD is measure of Voice Deepening;
SHL is a measure of Scalp Hair Loss;
FAI(T) is the Free Androgen Index measured at time T; in one embodiment, FAI is given by $$FAI(T) = 100 \times TT / SHBG \quad \text{Formula 4}$$

wherein the variables are measured at time T and
TT is the patient's Total Testosterone level and
SHBG is the patient's Sex Hormone Binding Globulin level;
TD is the dose of Androgenic Agent being administered at the same time as the AD dose.
BS is a measure of Breast Stiffness averaged across both breasts; and
SAL(T) is the Serum Aromatase Level of measured in ng/ml at time T; and wherein each parameters is measured just prior to the dose number N, except for FAI(T), AI(T) and SAL(T), which are calculated at specified times T related to the dose number N.

In certain embodiments, H, A, VD and SHL are measured on a baseline visual analog scale of 0 to 100 mm. In certain embodiments, BS is measured in Newtons per centimeter using the algorithm of Boyd et al. (2014).

F1 is a drug specific function having the following characteristics: (1) F1 is non-increasing in the following parameters: BW, TBF, AGE (wherein non-increasing is understood to mean, for example, if the other parameters are held constant and BW is increased then the resulting AD calculated with F1 will either stay the same or decrease), and/or (2) F1 is non-decreasing in MBD, BS (wherein non-decreasing is understood to mean, for example, if the other parameters are held constant and BS is increased then the resulting AD calculated with F1 will either stay the same or decrease).

F2 is a drug specific function having the following characteristics: (1) F2 is a non-increasing function of AGE; and/or (2) F2 is a non-decreasing function of BW, TBF, MBD, BS.

F3 is an increasing function of H, A, VD and SHL.

In certain embodiments, one or more functional forms of F1, F2 and F3 may provide acceptable dosages when calibrated to the pharmacokinetic and other characteristics of the specifically chosen androgenic agent and aromatase inhibitor.

In one embodiment the following functional forms have been proven effective where the androgenic agent is testosterone (T) and the aromatase inhibitor (Ai) is Anastrozole and doses are given at 4 monthly intervals:

F1:

$$AD=V1(N) \times (C1 \times 1/BW \times 1/TBF \times MBD + C2 \times (C3/AGE) + V2(N)) \quad \text{Formula 1A}$$

wherein MBD is the average for both breasts of the percentage of breast fibro-glandular tissue relative to total breast volume and C1, C2 and C3 are constants and V1(N) and V2(N) are defined below;

F2:

$$TD=V1(N) \times (C4 \times BW \times TBF \times MBD + C5 \times (C3-AGE) + V3(N)) \quad \text{Formula 2A}$$

wherein C4 and C5 are constants and V3(N) is described below; and

F3:

$$AI=(H+A+VD+SHL)/4 \quad \text{Formula 3A}$$

wherein H, A, VD and SI-IL are measured on a baseline visual analog scale of 0 to 100 mm and then reevaluated at the one year MBD measurement.

In certain embodiments, one or more of these parameters are optimised according to the individual patient to achieve the following optimal outcomes on average: FAI of 15% at one month after a dose and 5% at 3 months after a dose; and/or SAL of 35 ng/ml at 1 month after a dose and 25 ng/ml at 3 months after a dose.

In certain embodiments, one or more of these parameters are optimised according to the individual patient to achieve the following optimal outcomes on average: FAI of 15% at one month after a dose and 5% at 3 months after a dose; and/or SAL of 35 ng/ml at 1 month after a dose and 25 ng/ml at 3 months after a dose; wherein a reduction of MBD of at least 2% per annum is constrained by the dose of the AI not increasing more than 10% in that year.

Using the above dosing functional forms as a starting point and known pharmacokinetic and activity profile differences, the constants in the functional forms or the functional forms may be adjusted to provide a starting point for adjusting constants to achieve the optimal outcomes specified above when using different aromatase inhibitors and androgenic agents.

The subsequent dosing is modified by reference to the following serum levels achieved:

TD increase or decrease (V3(N) in the above) in 4 month dosage is determined by achieving the optimal 1 month FAI of 15% and 3 months FAI of 5% such that the mg dosage of TD is +/−4 mg for each FAI % point above or below 10 (i.e. 1 month FAI-3 month FAI).

AD increase or decrease (V2(N) in the above) in 4 month dosage is determined by achieving an optimal serum anastrozole level of 35 ng/ml at 1 month and 25 ng/ml at 3 months such that AD is increased or decreased 0.1 mg for each ng/ml above or below the 10 (i.e. 1 month serum anastrozole level-3 month serum anastrozole level)

Annual mammographic screening of density may be undertaken to determine reduction in breast density utilizing an appropriate mammographic algorithm that measures the volume of fibro-glandular tissue as percentage of total breast volume (MBD). The objective is to achieve MBD of less than 10% when this is a function of the average of both breast densities. The rate of breast density reduction should be at least 2% per annum. An annual uplift factor (V1(N) in the above) may be introduced into TD and AD of 10% of dosing if 2% is not achieved in the first year. This annual uplift factor typically will only be introduced, on an annual bassis, if there is less than 10% increase in androgenicity index (AI) defined as the following.

In certain embodiments, dosage levels below the lower limit of the aforesaid range of the aromatase inhibitor may be more than adequate, while in other cases still larger doses above the upper limit of the aforesaid range may be employed without causing harmful side effects. For example, dosages of an aromatase inhibitor above the upper limit may be used to improve the bioavailability of an androgenic agent, such as testosterone or dihydrotestosterone, as described herein.

Testosterone naturally is not highly absorbed because it is broken down approximately 85% in the intestines by aromatase and other metabolic pathways into by-products such as inactive testosterone and dihydrotestosterone. The administration of an aromatase inhibitor in combination with testosterone, however, results in an increased absorption, and subsequently greater bioavailability.

In certain embodiments, the administration of an aromatase inhibitor in combination with testosterone results in an improvement in the bioavailability of testosterone between 10% to 50%, between 20% to 40%, or between 25% to 35%. In certain embodiments, the amount of increase in bioavailability of testosterone is greater than 15%, greater than 25%, greater than 30% or greater than 35%.

In certain embodiments, the administration of aromatase inhibitor in combination with testosterone results in an improvement in the bioavailability of dihydrotestosterone between 25% to 75%, between 35% to 65% or between 45% to 55%. In certain embodiments, the amount of increase in bioavailability of dihydrotestosterone is greater than 25%, greater than 35%, greater than 45% or greater than 55%.

In certain embodiments, the method may include administering a pharmaceutical composition comprising an androgenic agent and an aromatase inhibitor. The androgenic agent, for example, may be selected from the group consisting of testosterone, methyltestosterone, testosterone undecanoate, testosterone propionate, or a selective androgenic receptor modulator. In certain embodiments, the androgenic agent may be testosterone undecanoate, such as about 40 mg of testosterone undecanoate. The aromatase inhibitor, for example, may be selected from the group consisting of exemestane, formestane, anastrozole, letrozole, vorozole, or fadrozole. In certain aspects, the aromatase inhibitor may be anastrozole, such as about 1 mg of anastrozole. In certain embodiments, the method comprises administering a pharmaceutical composition comprising about 40 mg of testosterone undecanoate and about 1 mg of anastrozole.

In certain embodiments, the method may include administering a pharmaceutical composition comprising an androgenic agent linked to an aromatase inhibitor, e.g., via an ester linkage, or an androgenic agent/aromatase inhibitor complex, wherein the complex is created by methods in the art.

The route of administering an androgenic agent, an aromatase inhibitor, or a pharmaceutical composition comprising the androgenic agent and the aromatase inhibitor may be by one or more routes compatible with a desired outcome. For example, the routes of administration include orally (e.g., ingestion or inhalation), intraperitoneally, intradermally, transdermally, transmucosally, subcutaneously, sublingually, intravenously, intraarterially, intracavity, intracranially, intramuscularly, parenterally, or topically. In certain embodiments, the aromatase inhibitor and the androgenic agent are administered orally, transdermally, or subcutaneously.

The pharmaceutically acceptable agents are administered alone or in combination with pharmaceutically acceptable carriers, excipients, or diluents, and such administration may be carried out in single or multiple doses. The therapeutic agents may be administered in a wide variety of different dosage forms, i.e., they may be combined with various pharmaceutically acceptable inert carriers or excipients in the form of tablets, capsules, emulsions, lozenges, troches, hard candies, lollipops, powders, sprays, creams, salves, suppositories, jellies, gels, pastes, lotions, ointments, aqueous suspensions, injectable solutions, elixirs, syrups, injectable depots, implants, microencapsulated delivery systems, oil-based suspensions, and the like.

For example, androgenic agents may be administered by the aforementioned routes and dosage forms. In one embodiment, testosterone esters may be injected. These may include testosterone enanthate (Delatestryl) which is suspended in sesame oil, testosterone cypionate (Depo-Testosterone) which is suspended in cottonseed oil, testosterone propionate (Testovis; Virormone), testosterone phenylpropionate (Testolent), and a blend of four testosterone esters (Sustanon; Omnadren) which include testosterone propionate, testosterone phenylpropionate, testosterone isocaproate, and testosterone decanoate.

In another embodiment, testosterone may be injected as an aqueous suspension (Aquaviron). In another embodiment, testosterone may be administered via a transdermal patch (Androderm; Testoderm TTS). In another embodiment, testosterone may be administered by a gel (Androgel; Testim). In another embodiment, methyltestosterone may be administered orally, e.g., tablet (Metesto, Methitest, Testred, Oreton Methyl, and Android). In another embodiment, testosterone undecanoate may be administered orally, e.g., tablet (Androxon, Understor, Restandol, and Restinsol). In one embodiment, testosterone may be administered buccally (Striant). In another embodiment, testosterone may be administered subcutaneously, e.g., pellet (Testopel).

In certain embodiments, the pharmaceutical combinations comprising an aromatase inhibitor in combination with an androgenic agent include administration of a single pharmaceutical dosage formulation which contains both substances, as well as administration of each agent in its own separate pharmaceutical dosage formulation.

In certain embodiments, both the androgenic agent (e.g., testosterone, methyltestosterone, testosterone undecanoate, testosterone propionate, or a selective androgenic receptor modulator), and the aromatase inhibitor (e.g., anastrozole, exemestane, or letrozole) are administered orally, e.g., tablet or capsule. For example, both testosterone and anastrozole are administered orally.

In some embodiments, both the androgenic agent (e.g., testosterone, methyltestosterone, testosterone undecanoate, testosterone propionate, or a selective androgenic receptor modulator), and the aromatase inhibitor (e.g., anastrozole, exemestane, or letrozole) are administered transdermally, e.g., patch. For example, both testosterone and anastrozole are administered transdermally.

In some embodiments, both the androgenic agent (e.g., testosterone, methyltestosterone, testosterone undecanoate, testosterone propionate, or a selective androgenic receptor modulator), and the aromatase inhibitor (e.g., anastrozole, exemestane, or letrozole) are administered subcutaneously, e.g., pellet. For example, both testosterone and anastrozole are administered subcutaneously.

Patient compliance is a factor in receiving a good result in medical treatment. Causes for poor compliance may include, but are not limited to, complicated regimen, unattractive and/or painful formulation such as needles, and physical difficulty in complying. Therefore, administration of two or even more different dosage forms to the patient may not be convenient or satisfactory to achieve the most optimal results. A pharmaceutical composition comprising an androgenic agent and aromatase inhibitor combined into a single dosage form may provide improved patient compliance.

Where separate dosage formulations are used, the aromatase inhibitor and the androgenic agent can be administered at essentially the same time (e.g., substantially at the same time, concurrently, or simultaneously) or at separately staggered times (e.g., sequentially). The pharmaceutical compositions disclosed herein are understood to include one or more these regimens. Administration of the pharmaceutical composition by the routes mentioned herein using a suitable regimen may be used as long as the beneficial pharmaceutical effect of the aromatase inhibitor and androgenic agent are realized by the patient. In certain embodiments, the aromatase inhibitor and androgenic agent may be administered concurrently on a once-a-day dosing schedule; however, varying dosing schedules, such as the aromatase inhibitor once per day and the androgenic agent once, twice or more times per day, or the androgenic agent once per day and the aromatase inhibitor once, twice or more times per day, is also encompassed herein. In certain embodiments, a single oral daily dosage formulation may be administered, comprising both the aromatase inhibitor and androgenic agent. A single dosage formulation may provide convenience for the patient.

The appropriate dosing regimen utilizing the androgenic agent, the aromatase inhibitor, or pharmaceutical compositions comprising the androgenic agent and the aromatase inhibitor, the amount of each dose administered, and the intervals between doses of the compounds may depend on various factors such as the particular aromatase inhibitor and androgenic agent being used in combination, the type of pharmaceutical formulation being used, the type of physiological condition being treated, the characteristics of the subject being treated (e.g., species, age, weight, sex, medical condition, fed/fasted), the route of administration, and the severity of the disorder being treated or combinations thereof. A physician or diagnostician of ordinary skill can readily determine and prescribed the effective amount of the androgenic agent, the aromatase inhibitor, or pharmaceutical composition to prevent or to treat the specific physiological condition.

Such pharmaceutical compositions, or individual androgenic agent and/or aromatase inhibitor, may be administered in a single daily dose, or the total daily dosage may be administered in divided doses several times daily. Furthermore, the pharmaceutical compositions, or individual androgenic agent and/or aromatase inhibitor, may be administered as a single dose or over a period of time. Additionally, the pharmaceutical compositions, or individual androgenic agent and/or aromatase inhibitor, may be administered continuously or intermittently. The daily dosage may be varied over wide range and can be such that the amount of the active compound selected from the androgenic agent and/or aromatase inhibitor is sufficient to cause its desired effects.

The pharmaceutical composition or formulation to be administered may contain a quantity of the compounds or pharmaceutically acceptable salts thereof in an amount effective to treat the condition of the subject being treated. Because two different compounds may be used together in a combination therapy, the potency of each of the compounds and the interactive effects achieved by combining them together typically will also be taken into account. A consideration of these factors is well within the purview of the ordinarily skilled clinician for the purpose of determining the therapeutically effective or prophylactically effective dosage amounts needed to improve side effects.

Administration of the androgenic agent, the aromatase inhibitor, or the pharmaceutical composition comprising a combination of the same, to the subject includes both self-administration and administration to the subject by another person (e.g., physician, nurse, health care worker, friend, etc.).

In certain embodiments, the pharmaceutical compositions may be formulated in a manner compatible with a desired outcome. The pharmaceutical compositions may be administered in a convenient formulation. The following formulation examples only are illustrative and are not intended to limit the scope of the present disclosure.

In certain embodiments, the pharmaceutical compositions may be formulated into tablets, such as those prepared by direct compression, by wet granulation, or by dry granulation. For example, the tablet formulations may incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders. A lubricant may be necessary in a tablet formulation to prevent the tablet and punches from sticking in the die. The lubricant is chosen from such slippery solids as talc, magnesium and calcium stearate, stearic acid and hydrogenated vegetable oils. Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate. Also, super disintegrants including, but not limited to, Ac-Di-Sol® (sodium croscarmellose cellulose), Explotab® (sodium starch glycolate), VivaStarg (sodium starch glycolate), and Polyplasdone disintegrants may be used.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients. The size and shape of the tablet may vary according to standard dimensions and shapes known in the art.

In certain embodiments, the pharmaceutical compositions may be formulated into capsules, such as those prepared by mixing the compound with a suitable diluents and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders. The size and shape of the capsule may vary according to standard dimensions and shapes known in the art.

Furthermore, the capsule may be liquid-filled or non-liquid-filled. The capsule may be a hard or soft capsule. Furthermore, it may be a gelatin capsule, a starch capsule, a hydroxypropylmethylcellulose (HPMC) capsule, or a cellulosic capsule. Although not limited to capsules, such dosage forms can further be coated with, for example, a seal coating, an enteric coating, an extended release coating, or a targeted delayed release coating. Additionally, liquid-filled capsules may be emulsions and/or may contain tocopherol as a carrier for poorly soluble compounds such as testosterone.

In certain embodiments, tocopherol may be used as the hydrophobic dispersed phase of an emulsion containing water insoluble, poorly water soluble therapeutic agents, water soluble ones which have been modified to be less water soluble, or mixtures thereof. In a preferred aspect alpha-tocopherol is employed. Alpha-tocopherol is secreted by the enterocytes into the lymphatics and is processed in a similar manner to other forms of vitamin E. Also called vitamin E, alpha-tocopherol is not typical lipid oil. It has a higher polarity than most lipid oils, particularly triglycerides, and is not saponifiable. It has practically no solubility in water.

In certain embodiments, an alpha-tocopherol emulsion in the form of a self-emulsifying system may be used, where the system is to be used for the oral administration of water-insoluble (or poorly water-soluble or water-soluble agents modified to be less water soluble or mixtures thereof) drugs where that is desired. In such embodiments, an oil phase with surfactant and drug or drug mixture is encapsulated into a soft or hard gelatin capsule. Suitable solidification agents with melting points in the range of 40 to 60° C., such as high molecular weight polyethylene glycols (MW>1000), and glycerides, such as those available under the trade name Gelucire (Gattefose Corp., Saint Priest, France), can be added to allow filling of the formulation into a hard gelatin capsule at a high temperature. Semi-solid formulations are formed upon room temperature equilibration. Upon dissolution of the gelatin in the stomach and duodenum, the oil is released and forms a fine emulsion with a mean droplet diameter of between about 1 to about 15 microns, between about 2 to about 10 microns, or between about 2 to about 5 microns spontaneously. The emulsion is then taken up by the microvilli of the intestine and released into the bloodstream.

In certain embodiments, microemulsions containing tocopherol, preferably alpha-tocopherol, may be used. Microemulsions refer to a sub-class of emulsions where the emulsion suspension is essentially clear and indefinitely stable by virtue of the extremely small size of the oil/drug microaggregates dispersed therein.

In certain embodiments, PEGylated vitamin E (alpha-tocopheryl polyethylene glycol succinate, abbreviated TPGS) may be used as a primary surfactant in emulsions of vitamin E. TPGS is utilized as a primary surfactant, a stabilizer and also as a supplementary solvent in emulsions of vitamin E. TPGS is a water-soluble derivative of d-alpha-tocopheryl succinate. It is also used as an absorption and bioavailability enhancer for certain water-insoluble drugs (e.g. the HIV protease inhibitor amprenavir) and fat-soluble vitamins such as vitamin D. TPGS, because of its amphipathic nature (has both hydrophilic and lipophilic ends), forms its own micelles and thus does not require bile salts to do so. This makes it an excellent alpha-tocopherol substance for those who have problems secreting bile salts into the intestine (e.g., those with chronic childhood cholestasis).

TPGS may enhance the absorption of lipophilic drugs if formulated together with them. For this reason, the HIV protease inhibitor amprenavir is formulated with TPGS. Further, the enhancement of the oral bioavailability of some drugs when co-administered with TPGS may, in part, be due to inhibition of P-glycoprotein in the intestine. P-glycoprotein is the multidrug resistance transporter and is involved in the mediation of multidrug resistance.

In addition, polyethylene glycol (PEG) is also useful as a co-solvent in the emulsions disclosed herein. Of particular use is polyethylene glycol 200, 300, 400 or mixtures thereof.

The alpha-tocopherol concentration of the emulsions may be between about 1 to about 10% w/v, between about 2 to about 5% w/v, or between about 3 to about 4% w/v. The ratio of alpha-tocopherol to TPGS is optimally between about 1:1 to about 10:1 (w/w), between about 1:1 to about 5:1 (w/w), or between about 1:1 to about 15:1 (w/w).

The emulsions disclosed herein may further include surfactants such as ascorbyl-6 palmitate, stearylamine, PEGylated phospholipids, sucrose fatty acid esters and various vitamin E derivatives comprising Q-tocopherol nicotinate, tocopherol phosphate, and nonionic, synthetic surfactant mixtures, such as polyoxypropylene-polyoxyethylene glycol nonionic block copolymer.

The emulsions disclosed herein may comprise an aqueous medium. The aqueous phase generally has an osmolality of approximately 300 mOsm and may include sodium chloride, sorbitol, mannitol, polyethylene glycol, propylene glycol albumin, polypep and mixtures thereof. Osmolality may also range between about 100 to about 500 mOsm and between about 200 to about 400 mOsm. This medium can also contain various additives to assist in stabilizing the emulsion or in rendering the formulation biocompatible. Acceptable additives include acidifying agents, alkalizing agents, antimicrobial preservatives, antioxidants, buffering agents, chelating agents, suspending and/or viscosity-increasing agents, and tonicity agents. Preferably, agents to control the pH, tonicity, and increase viscosity are included. Optimally, a tonicity of at least 250 mOsm is achieved with an agent which also increases viscosity, such as sorbitol or sucrose. Tonicity may also be of at least 300 mOsm, at least 400 mOsm, or at least 500 mOsm.

The emulsions disclosed herein for intravenous injection have a particle size (mean droplet diameter) of about 10 to about 500 nm, preferably about 10 to about 200 nm and most preferably about 10 to about 100 nm. For intravenous emulsions, the spleen and liver typically will eliminate particles greater than 500 nm in size through the RES.

Also testosterone within a liquid-capsule emulsion system may be used.

Aqueous suspensions and/or elixirs are prepared by combining the active ingredient with various sweetening or flavoring agents, coloring matter or dyes, and, if so desired, emulsifying and/or suspending agents as well, together with such diluents as water, ethanol, propylene glycol, glycerin and various like combinations thereof. The amount of suspension may vary according to standard volumes known in the art.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate. For example, to formulate duloxetine and duloxetine-containing combinations as enteric compositions. Another example is to formulate them as enteric pellets. The size and shape of such formulations may vary according to standard dimensions and shapes known in the art.

Transdermal patches may also be used. Transdermal administration significantly enhances patient compliance by alleviating the discomfort of needles and other dosage forms by providing a convenient dosage form for once or twice weekly application. Such administration also provides the benefit of having sustained blood levels of the drug being adminstered. Typically patches comprise a resinous composition in which the drugs will dissolve, or partially dissolve, which is held in contact with the skin by a film which protects the composition. Other, more complicated patch compositions are also in use, particularly those having a membrane pierced with innumerable pores through which the drugs are pumped by osmotic action. The size of the patch may vary according to sizes known in the art.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are also in wide use.

For parenteral, intradermal, intramuscular, or subcutaneous administration, the pharmaceutical compositions may include one of the following, or any combination thereof: a sterile diluents, such as water, saline solution, fixed oils, polyethylene glycols, glycerine, propylene glycol or other synthetic solvents; surfactants such as polysorbate 80, sodium lauryl sulfate, sorbitan monopalmitate; alcohols; suspending agent such as agar, bentonite, microcrystalline cellulose, sodium carboxymethylcellulose, hydroxypropyl methylcellulose, tragacanth, veegum; antibacterial agents such as benzyl alcohol or methyl parabens; antioxidants such as ascorbic acid or sodium bisulfate; chelating agents such as ethylenediaminetetraacetic acid; and buffers such as acetates, citrates or phosphates and agents for the adjustment of tonicity such as sodium chloride or dextrose.

In certain embodiments, the pharmaceutical compositions administered may also include carriers to protect the composition against rapid degradation or elimination from the body, such as a controlled release or sustained release or extended release formulation, including implants and microencapsulated delivery systems. For example, a time delay material such as glyceryl monostearate or glyceryl stearate alone, or in combination with a wax, may be employed. Also, pharmaceutical compositions can include excipients that modify gut metabolism.

Additional methods of preparing various pharmaceutical compositions with a certain amount of each active ingredient are known, or will be apparent in light of this disclosure, to those skilled in this art.

In certain embodiments, the methods may also include the administering to the patient the androgenic agent, the aromatase inhibitor, or pharmaceutical composition comprising a combination of the same, in the form of an article of manufacture, such as a kit, which includes the active ingredients disclosed herein, or the active ingredients in suitable pharmaceutical compositions, packaged for distribution. Kits may additionally include instructions for using the kit components in one or more of the disclosed methods. Instructions may include instructions for practicing one or more of the disclosed methods. Thus, for example, a kit can include an androgenic agent or an aromatase inhibitor in a pharmaceutical formulation in a container, pack, or dispenser together with instructions for administration to a human subject.

Instructions may additionally include indications of a satisfactory clinical endpoint or any adverse symptoms that may occur, or any additional information required by the Food and Drug Administration for use in humans.

The instructions may be on "printed matter," e.g., on paper or cardboard within the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM, and hybrids of these such as magnetic/optical storage media.

Kits can additionally include a buffering agent, a preservative, or a stabilizing agent. Each component of the kit can be enclosed within an individual container and all of the various containers can be within a single package.

Since certain embodiments, relate to providing a combination of the two active ingredients which may be administered separately, the present disclosure also relates to combining separate pharmaceutical compositions in kit form. The kit includes two separate pharmaceutical compositions: an androgenic agent and an aromatase inhibitor. The kit includes a container for containing the separate compositions such as a divided bottle or a divided foil packet, however, the separate compositions may also be contained within a single, undivided container. Typically the kit includes directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of a kit is a so-called blister pack. Blister packs are well known in the packaging industry and are being widely used for the packaging of pharmaceutical unit dosage forms (e.g., tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on a card insert, e.g., in the form of numbers next to the tablets or capsules whereby the numbers correspond with the days of the regimen which the tablets or capsules so specified should be administered. Another example of such a memory aid is a calendar printed on the card. Other variations of memory aids will be readily apparent.

Packaging may be accomplished by a number of means utilized in the pharmaceutical industry. Examples of such packaging are: unit dose containers for dispensing liquid compositions enclosed in a box or container along with package inserts; plastic and/or foil wrappers holding solid ocular inserts which contain the active ingredients of the invention and which are enclosed in a box or container along with package inserts. Other modes of packaging would be readily apparent to one skilled in the pharmaceutical packaging arts.

While the present disclosure has been described in terms of certain exemplary embodiments in order to facilitate better understanding of the present disclosure, it should be appreciated that various modifications can be made without departing from the principles of the disclosed herein. Therefore, the inventions should be understood to include such modifications within its scope.

EXAMPLES

Example 1

Figure 2:
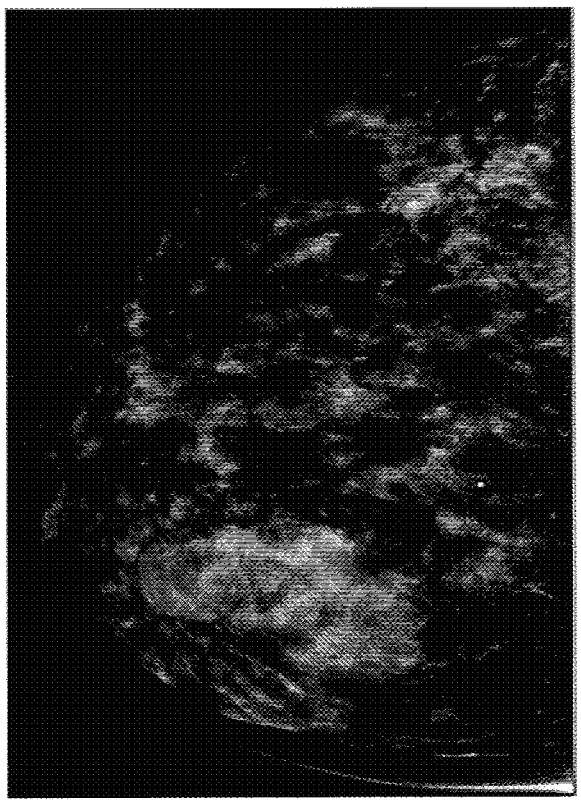
FIG. 2 is a mammogram of the patient's breast at 1 year, i.e., after 1 year of treatment), according to certain embodiments.

A 50 year old woman with high mammographic breast density was treated with a subcutaneous pellet containing the combination of a testosterone and anastrozole for menopausal symptoms including painful breast cysts using the following dosing algorithm. After 1 year of treatment, an improvement in MBD was observed by mammographaphy (FIG. 1 was the mammogram of the patient's breast immediately before treatment, and FIG. 2 was the mammogram of the patient's breast at 1 year, i.e., after 1 year of treatment).

FAI is calculated from a formula where the serum measurement of total testosterone and sex hormone binding globulin are calculated by radio immunoassay. Aromatase inhibitor serum level is determined by liquid chromatography-tandem mass spectrometry.

Dose Schedule
Initial Dosing $$\text{Initial dosing (androgenic agent): TD}=\text{BW}\times TBF\times \text{MBD}+(100-\text{AGE})$$

$$\text{Testosterone } 59 \text{ mg}=75\times 0.4\times 0.3+50$$

$$\text{Initial dosing (aromatase inhibitor): AD}=1/\text{BW}\times 1/TBF\times \text{MBD}+(100/\text{AGE})$$

$$\text{Anastrozole } 2.75 \text{ mg}=1/75\times 1/0.4\times 0.3+100/50$$

Pellet 1: FAI 15.5% 1 month
FAI 2.5% 3 months
Serum Anastrozole 1 month 38 ng/ml
Serum Anastrozole 3 month 28 ng/ml
Second Dosing at 4 months $$\text{Testosterone } 71 \text{ mg}=(75\times 0.4\times 0.3+50)+((13-10)\times 4)$$

$$\text{Anastrozole } 2.75 \text{ mg}=1/75\times 1/0.4\times 0.3+100/50+((10-10)\times 4)$$

Pellet 2 FAI 16.5% 1 month
FAI 6.5% 3 months
Serum Anastrozole 1 month 35 ng/ml
Serum Anastrozole 3 month 25 ng/ml
Third Dosing at 8 months $$\text{Testosterone } 71 \text{ mg}=(75\times 0.4\times 0.3+50)+((10-10)\times 4)$$

$$\text{Anastrozole } 2.75 \text{ mg}=1/75\times 1/0.4\times 0.3+100/50+((10-10)\times 4)$$

Pellet 3 FAI 16.5% 1 month
FAI 6.5% 3 months
Serum Anastrozole 1 month 38 ng/ml
Serum Anastrozole 3 month 28 ng/ml
Fourth Dosing at 12 months with a 15% reduction in MBD (see below) and:

$$\text{Baseline AI}=(H+A+\text{VD}+\text{SHL})/4(21+0+0+0)=5.2$$

$$1 \text{ Year AI}=(H+A+\text{VD}+\text{SHL})/4(20+0+0+0)=5$$

Therefore as the AI has not increased above 10% and the 15% reduction is well above the target of 2% no dosage alteration is required.

Testosterone 54.5 mg=(75×0.4×0.15+50)+((10−10)× 4)

Anastrozole 2.05 mg=1/75×1/0.4×0.15+100/50+((10− 10)×4)

Example 2

Thirty women with MDB have been treated over the past 18 months with 20 having had 2 mammograms for evaluations at baseline and 1 year (Table 1).

TABLE 1

|  | Baseline median (range) | One year median (range) |
|---|---|---|
| Age | 48 (41-56) |  |
| MBD (%) | 35 (20-45) | 25 (13-32) |
|  | 1$^{st}$ 3 month trough | End 1st year 3 month trough |
| FAI (%) | 4.8 (2-4.9) | 5.9 (2.1-6.5) |
| Serum anastrozole (ng/ml) | 27 (22-39) | 32 (22-39) |

8 women have been evaluated for breast stiffness in regard to breast pain reduction.

A 100 mm Visual Analogue Scale assessed breast pain at baseline and 1 year follow-up mammogram (Table 2). The formulas discussed in Example 1 were utilized to assess breast stiffness.

TABLE 2

|  | Baseline median (range) | One year median (range) |
|---|---|---|
| Age | 44 (41-47) |  |
| MBD (%) | 36 (29-44) | 21 (13-30) |
| VAS breast pain (mm) | 75 (60-100) | 30 (0-50) |
| Breast Stiffness (N/cm) | 45 (38-48) | 25 (18-31) |

Example 3

A patient having a mammographic breast density of at least 7.5%, is given an initial dose of both an androgenic agent and an aromatase inhibitor in a subcutaneous pellet, wherein the initial doses are determined by the treating physician according to standard doses for each specific agent. The subsequent doses of the androgenic agent and aromatase inhibitor in subcutaneous pellets, each measured in mg, are provided every 3 months to the patient and are determined as a function of the following formulas:

$$AD=F1(N,T,BW,TBF,MBD,BS,AGE,FAI(T),AI(T),TD) \quad \text{Formula 1}$$

$$TD=F2(N,T,BW,TBF,MBD,BS,AGE,SAL(T),AI(T)) \quad \text{Formula 2}$$

wherein:
N is the dose number (N=1 being the first dose);
T is time in months from the first dose;
BW is body weight measured in kg;
TBF is fraction of BW measured by bio-impedance;
MBD is mammographic breast density, being the percentage of breast fibro-glandular tissue relative to total breast volume where the MBD is the average of both breasts, e.g., measured by Volpara breast density software;
Age=years;
AI(T) is the Androgenicity Index as a function of time which is given by:

$$AI(T)=F3(H,A,VD,SHL) \quad \text{Formula 3}$$

wherein each of the parameters is measured at time T and
H is a measure of Hirutism;
A is a measure of Acne;
VD is measure of Voice Deepening;
SHL is a measure of Scalp Hair Loss;
FAI(T) is the Free Androgen Index measured at time T; In one embodiment. FAI is given by $$FAI(T)=100\times TT/SHBG \quad \text{Formula 4}$$

wherein the variables are measured at time T and
TT is the patient's Total Testosterone level and
SHBG is the patient's Sex Hormone Binding Globulin level;
TD is the dose of Androgenic Agent being administered at the same time as the AD dose.
BS is a measure of Breast Stiffness averaged across both breasts; and
SAL(T) is the Serum Aromatase Level of measured in ng/ml at time T; and wherein each parameters is measured just prior to the dose number N, except for FAI(T), AI(T) and SAL(T), which are calculated at specified times T related to the dose number N.

Accordingly, using Formulas 1A and 2A along with the data from Example 1, the following parameters include possible alternative values as determined by the individual patient:

$V1(N)=1$ for $N=1,2,3$ $V1(4\times n)=(1+R(n))\times V1(4\times n-1)$ for $n=1,2,3\ldots$ $V1(4\times n+m)=V1(4\times n)$ for $m=1,2,3$ and $n=1,2,3\ldots$ where $R(n)=0$ if $AI(12\times n)-AI(0)>C6$ $R(n)=0$ if $MBD(4\times n-3)-MBD(4\times n)>C12$ $R(n)=0$ if $1-BS(4\times n)/BS(2\times n-3)>C13$ otherwise $R(n)=C7$.

$V2(1)=0$ $V2(N)=C10\times(SAL(4\times(N-1)-3)-SAL(4\times(N-1)-1)-C11)$ for $N>1$ $V3(1)=0$ $V3(N)=C8\times(FAI(4\times(N-1)-3)-FAI(4\times(N-1)-1)-C9)$ for $N>1$ C1 to C12 are constants and in one embodiment are given by:
C1=C2=C4=C5=1
C3=100 years
C6=10%
C7=0.1
C8=4 mg
C9=10
C10=0.1 mg
C11=10 ng/ml
C12=2%
C13=20%.

The above parameters are then optimised to achieve the following optimal outcomes on average:

FAI of 15% at one month after a dose and 5% at 3 months after a dose;

SAL of 35 ng/ml at 1 month after a dose and 25 ng/ml at 3 months after a dose;

A reduction of 2% per annum in the MBD constrained by the AI not increasing more than 10% in that year.

In the following, further embodiments are explained with the help of subsequent examples.

Example A1

A method of treating mammographic breast density and/or breast stiffness in a patient in need thereof, comprising administering to the patient;
i) an effective amount of androgenic agent; and
ii) an effective amount of an aromatase inhibitor.

Example A2

A method of treating mammographic breast density and/or breast stiffness in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A3

A method of treating mammographic breast density in a patient having a breast with a BIRADS score of 3 or 4 (or e or d), comprising administering to the patient:
i) an effective amount of androgenic agent; and
ii) an effective amount of an aromatase inhibitor.

Example A4

A method of treating mammographic breast density in a patient having a breast with a BIRADS score of 3 or 4 (or c or d), comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A5

A method of reducing mammographic breast density in a patient having a breast with a mammographic breast density of 7.5% or greater, comprising administering to the patient:
i) an effective amount of androgenic agent; and
ii) an effective amount of an aromatase inhibitor.

Example A6

A method of reducing mammographic breast density in a patient having a breast with a mammographic breast density of 7.5% or greater, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A7

A method of inducing breast involution in a patient in need thereof, comprising administering to the patient:
i) an effective amount of androgenic agent; and
ii) an effective amount of an aromatase inhibitor.

Example A8

A method of inducing breast involution in a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A9

A method of inducing net cell death over proliferation in a breast of a patient in need thereof, comprising administering to the patient:
i) an effective amount of androgenic agent; and
ii) an effective amount of an aromatase inhibitor.

Example A10

A method of inducing net cell death over proliferation in a breast of a patient in need thereof, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A11

A method of reversing cell number and mammographic breast density in a breast of a peri-menopausal patient, comprising administering to the patient:
i) an effective amount of androgenic agent; and
ii) an effective amount of an aromatase inhibitor.

Example A12

A method of reversing cell number and mammographic breast density in a breast of a peri-menopausal patient, comprising administering to the patient a pharmaceutical composition comprising:
i) an effective amount of androgenic agent;
ii) an effective amount of an aromatase inhibitor; and
iii) optionally, a pharmaceutically acceptable excipient and/or carrier.

Example A13

A method of reducing mammographic breast density and peri-menopausal symptoms in a patient in need thereof, comprising administering to the patient:
i) an effective amount of androgenic agent; and
ii) an effective amount of an aromatase inhibitor.

Example A14

A method of reducing mammographic breast density and peri-menopausal symptoms in a patient in need thereof, comprising administering to the patient a pharmaceutical composition comprising:
  i) an effective amount of androgenic agent;
  ii) an effective amount of an aromatase inhibitor; and
  iii) optionally, a pharmaceutically acceptable excipient and/or carrier.

Example A15

A method of reducing breast stiffness in a patient in need thereof, comprising administering to the patient:
  i) an effective amount of androgenic agent; and
  ii) an effective amount of an aromatase inhibitor.

Example A16

A method of reducing breast stiffness in a patient in need thereof, comprising administering to the patient a pharmaceutical composition comprising:
  i) an effective amount of androgenic agent;
  ii) an effective amount of an aromatase inhibitor; and
  iii) optionally, a pharmaceutically acceptable excipient and/or carrier.

Example A17

The method of any one of Examples A 1-16, wherein the androgenic agent is a selective androgenic receptor modulator.

Example A18

The method of any one of Examples A1-17, wherein the method further comprises:
  a) measuring free androgenic index levels and/or aromatase inhibitor levels in serum isolated from a blood sample taken from the patient after at least 1 month of treatment;
  b) determining a subsequent dose, comprising a subsequent effective amount of androgenic agent and a subsequent effective amount of an aromatase inhibitor; and
  c) administering to the patient the subsequent dose.

Example A19

The method of any one of Examples A 1-18, wherein the method further comprises:
  a) measuring free androgenic index levels and/or aromatase inhibitor levels in serum isolated from a blood sample taken from the patient after at least 1 month of treatment, comprising centrifuging the patient's blood sample to isolate the serum;
  b) determining a subsequent dose, comprising a subsequent effective amount of androgenic agent and a subsequent effective amount of an aromatase inhibitor; and
  c) administering to the patient the subsequent dose.

Example A20

The method of any one of Examples A1-19, wherein the patient's breast has a BIRADS score of 3 or 4 (or c or d).

Example A21

The method of any one of Examples A1-20, wherein the patient's breast has a BIRADS score of 4 (or d).

Example A22

The method of any one of Examples A1-21, wherein the patient's breast has a mammographic breast density of 7.5% or greater.

Example A23

The method of any one of Examples A1-22, wherein the patient's breast has a mammographic breast density of 25% or greater.

Example A24

The method of any one of Examples A1-23, wherein the patient's breast has a mammographic breast density of 50% or greater.

Example A25

The method of any one of Examples A1-24, wherein the patient's breast is a mammographically dense breast.

Example A26

The method of any one of Examples A1-25, wherein the patient's breast has the same or more breast tissue than fat.

Example A27

The method of any one of Examples A1-26, wherein the patient's breast has more breast tissue than fat.

Example A28

The method of any one of Examples A1-27, wherein the method reduces or decreases the patient's BIRADS score between 1 or more annual intervening mammographic detections.

Example A29

The method of any one of Examples A1-28, wherein the method maintains or stabilizes the patient's BIRADS score between 1 or more annual intervening mammographic detections.

Example A30

The method of any one of Examples A1-29, wherein the patient's BIRADS score reduces or decreases by 2 or more.

Example A31

The method of any one of Examples A1-30, wherein the patient's BIRADS score reduces or decreases by 3 or 4.

Example A32

The method of any one of Examples A1-31, wherein the patient's BIRADS score reduces or decreases by 4.

Example A33

The method of any one of Examples A1-32, wherein the patient is peri-menopausal.

Example A34

The method of any one of Examples A1-33, wherein the patient is post-menopausal.

Example A35

The method of any one of Examples A1-34, wherein the method reduces or decreases the mammographic breast density of the patient's breast between one or more annual intervening mammographic detections.

Example A36

The method of any one of Examples A1-35, wherein the mammographic breast density reduces by at least 2% per annum.

Example A37

The method of any one of Examples A1-36, wherein the mammographic breast density reduces by at least 8% per annum.

Example A38

The method of any one of Examples A1-37, wherein the mammographic breast density reduces by at least 30% per annum.

Example A39

The method of any one of Examples A1-38, wherein the mammographic breast density reduces or decreases 20-40% per annum.

Example A40

The method of any one of Examples A 1-39, wherein the reduction or decrease in the mammographic breast density is in the range of between 1% to 99%.

Example A41

The method of any one of Examples A1-40, wherein the reduction or decrease in the mammographic breast density is in the range of between 10% to 90%.

Example A42

The method of any one of Examples A1-41, wherein the reduction or decrease in the mammographic breast density is in the range of between 1% to 50%.

Example A43

The method of any one of Examples A1-42, wherein the method maintains or stabilizes the mammographic breast density of the patient's breast between one or more annual intervening mammographic detections.

Example A44

The method of any one of Examples A1-43, wherein the method reduces or decreases the breast stiffness of the patient's breast between one or more annual intervening mammographic detections.

Example A45

The method of any one of Examples A1-44, wherein the breast stiffness reduces by at least 5% per annum.

Example A46

The method of any one of Examples A1-45, wherein the breast stiffness reduces by at least 10% per annum.

Example A47

The method of any one of Examples A1-46, wherein the breast stiffness reduces by at least 25% per annum.

Example A48

The method of any one of Examples A1-47, wherein the breast stiffness reduces by at least 50% per annum.

Example A49

The method of any one of Examples A1-48, wherein the breast stiffness reduces or decreases 20-40% per annum.

Example A50

The method of any one of Examples A1-49, wherein the reduction or decrease in the breast stiffness is in the range of between 1% to 99%.

Example A51

The method of any one of Examples A1-50, wherein the reduction or decrease in the breast stiffness is in the range of between 10% to 90%.

Example A52

The method of any one of Examples A1-51, wherein the reduction or decrease in the breast stiffness is in the range of between 1% to 50%.

Example A51

The method of any one of Examples A1-52, wherein the method maintains or stabilizes the breast stiffness of the patient's breast between one or more annual intervening mammographic detections.

Example A54

The method of any one of Examples A1-53, wherein the mammographic breast density reduces by at least 2% per annum and the breast stiffness reduces by at least 10% per annum.

Example A55

The method of any one of Examples A1-54, wherein the method mitigates, reduces, or decreases, the treated patient's risk of developing breast cancer.

Example A56

The method of any one of Examples A1-55, wherein the method mitigates, reduces, or decreases, the treated patient's risk of developing breast cancer between one or more annual intervening mammographic detections.

Example A57

The method of any one of Examples A1-56, wherein the method mitigates, reduces, or decreases, the treated patient's risk of developing breast cancer and avoids, mitigates, reduces, or reverses one or more peri-menopausal symptoms.

Example A58

The method of any one of Examples A1-57, wherein the method enhances, increases, or improves, mammographic visualization or detection of the breast.

Example A59

The method of any one of Examples A1-58, wherein the method enhances, increases, or improves, the treated patient's fat to breast tissue ratio.

Example A60

The method of any one of Examples A1-59, wherein the patient's fat to breast tissue ratio increases in the range of between 1% to 99%.

Example A61

The method of any one of Examples A1-60, wherein the patient's fat to breast tissue ratio increases in the range of between 1% to 50%.

Example A62

The method of any one of Examples A1-61, wherein the patient's fat to breast tissue ratio increases in the range of between 3% to 20%

Example A63

The method of any one of Examples A1-62, wherein the method increases the percentage of fat in the treated patient's breast.

Example A64

The method of any one of Examples A1-63, wherein the method enhances, increases, or improves, breast compression during mammographic visualization or detection of the breast.

Example A65

The method of Example A64, wherein the method mitigates, reduces, or decreases, pain during the breast compression.

Example A66

The method of any one of Examples A1-65, wherein the method mitigates, reduces, or decreases, the treated patient's pain during mammographic visualization or detection of the breast.

Example A67

The method of Example A66, wherein the method enhances, increases, or improves, breast compression during the breast compression.

Example A68

The method of any one of Examples A1-67, wherein the method enhances, increases, or improves, the treated patient's compliance of having regular mammographic visualizations or detections.

Example A69

The method of any one of Examples A1-68, wherein the method mitigates, reduces, or decreases, the amount of radiation exposure required to visualize or detect the treated patient's breast during one or more subsequent mammographies.

Example A70

The method of any one of Examples A1-69, wherein the method induces breast involution.

Example A71

The method of any one of Examples A1-70, wherein the method induces involution of breast cells in the patient.

Example A72

The method of any one of Examples A1-71, wherein the method induces net cell death over proliferation in the breast of the patient.

Example A73

The method of any one of Examples A1-72, wherein the method reverses cell number and mammographic breast density in the breast of the peri-menopausal patient.

Example A74

The method of any one of Examples A1-73, wherein the treated patient has a free androgenic index level of 30% or greater within their breast within four hours of the administration of the androgenic agent and the aromatase inhibitor.

Example A75

The method of any one of Examples A1-74, wherein the treated patient has a supra-physiological free androgenic index level within their breast within four hours of the administration of the androgenic agent and the aromatase inhibitor.

Example A76

The method of any one of Examples A1-75, wherein the administration of the aromatase inhibitor reduces aromatization of testosterone to estrogen in the subcutaneous fat of the patient's breast by at least 80%.

Example A77

The method of any one of Examples A1-76, wherein the administration of the androgenic agent and the aromatase inhibitor is a co-administration.

Example A78

The method of any one of Examples A1-77, wherein the co-administration comprises concurrently, simultaneously, substantially at the same time, or sequentially.

Example A79

The method of any one of Examples A1-78, wherein the method reduces mammographic breast density and avoids inducing masculinizing androgenic side-effects or inducing a hyper-androgenic state.

Example A80

The method of any one of Examples A1-79, wherein the method reduces mammographic breast density and is exclusive of inducing masculinizing androgenic side-effects or inducing a hyper-androgenic state.

Example A81

The method of any one of Examples A1-80, wherein the method reduces mammographic breast density and minimizes induction of masculinizing androgenic side-effects or induction of a hyper-androgenic state.

Example A82

The method of any one of Examples A1-81, wherein the method provides one or more of the following:
 i) reduces mammographic breast density;
 ii) increases involutionary effects on the treated patient's breast without conversion of testosterone to estrogen;
 iii) reduces or reverses peri-menopausal symptoms; or
 iv) improves the treated patient's physical functioning, comprising cognitive function; reduction of a degenerative CNS disease, comprising dementia or parkinsonism; muscle strength; libido; energy; reduction of monoamine oxidase induced anxiety and depression; or combinations thereof.

Example A83

The method of any one of Examples A1-82, wherein the method provides one or more of the following:
 i) reduces mammographic breast density;
 ii) increases involutionary effects on hormonally affected end organs, comprising breast, without conversion of testosterone to estrogen;
 iii) reduces or reverses peri-menopausal symptoms related to fluctuating estrogen levels; or
 iv) improves the treated patient's physical functioning, comprising cognitive function; reduction of a degenerative CNS disease, comprising dementia or parkinsonism; muscle strength; libido; energy; reduction of monoamine oxidase induced anxiety and depression; or combinations thereof.

Example A84

The method of any one of Examples A1-83, wherein the method substantially reduces or reverses peri-menopausal symptoms.

Example A85

The method of any one of Examples A1-84, wherein the method substantially improves the treated patient's physical functioning.

Example A86

The method of any one of Examples A1-85, wherein the method substantially reduces or reverses peri-menopausal symptoms related to fluctuating estrogen levels.

While certain embodiments have been shown and described herein, it will be obvious to those skilled in the art that such embodiments are provided by way of example only. It is intended that the following claims define the scope of the inventions and that methods and structures within the scope of these claims and their equivalents be covered thereby.

What is claimed is:

1. A method of treating mammographic breast density and/or breast stiffness in a patient in need thereof, comprising administering to the patient a subcutaneous implant comprising:
 i) an effective amount of testosterone; and
 ii) 0.1-4 mg of anastrozole.

2. The method of claim 1, wherein the patient is peri-menopausal.

3. The method of claim 1, wherein the patient's breast has a mammographic breast density of 25% or greater.

4. The method of claim 1, wherein the method enhances, increases, or improves, mammographic visualization or detection of the breast.

5. The method of claim 1, wherein the method enhances, increases, or improves, breast compression during mammographic visualization or detection of the breast.

6. The method of claim 1, wherein the method enhances, increases, or improves, the treated patient's compliance of having regular mammographic visualizations or detections.

7. The method of claim 1, wherein the subcutaneous implant comprises:
 i) 50-150 mg of the testosterone; and
 ii) 1 mg, 2 mg, or 3 mg of the anastrozole.

8. The method of claim 7, wherein the patient is premenopausal.

9. The method of claim 7, wherein the patient is peri-menopausal.

10. The method of claim 7, wherein the patient is post-menopausal.

11. The method of claim 7, wherein the patient's breast has a BIRADS score of 3 or 4 (or c or d).

12. The method of claim 7, wherein the patient's breast has a mammographic breast density of 7.5% or greater.

13. The method of claim 7, wherein the method reduces or decreases the mammographic breast density of the patient's breast between one or more annual intervening mammographic detections.

14. The method of claim 7, wherein the method reduces or decreases the breast stiffness of the patient's breast between one or more annual intervening mammographic detections.

* * * * *